US010556848B2

(12) United States Patent
Leclerc et al.

(10) Patent No.: US 10,556,848 B2
(45) Date of Patent: Feb. 11, 2020

(54) SYSTEMS AND METHODS USING LANTHANIDE HALIDE

(71) Applicant: Calera Corporation, Moss Landing, CA (US)

(72) Inventors: Margarete K Leclerc, Mountain View, CA (US); Emily A Cole, Monterey, CA (US); Thomas A Albrecht, Santa Clara, CA (US); Michael Kostowskyj, Aptos, CA (US); Ryan J Gilliam, San Jose, CA (US); Michael J Weiss, Los Gatos, CA (US); Kyle Self, San Jose, CA (US)

(73) Assignee: Calera Corporation, Moss Landing, CA (US)

( * ) Notice: Subject to any disclaimer, the term of this patent is extended or adjusted under 35 U.S.C. 154(b) by 0 days.

(21) Appl. No.: 16/135,357

(22) Filed: Sep. 19, 2018

(65) Prior Publication Data

US 2019/0119186 A1 Apr. 25, 2019

Related U.S. Application Data

(60) Provisional application No. 62/560,363, filed on Sep. 19, 2017.

(51) Int. Cl.
*C07C 17/013* (2006.01)
*C07C 17/02* (2006.01)
(Continued)

(52) U.S. Cl.
CPC ............. *C07C 17/02* (2013.01); *C07C 17/013* (2013.01); *C07C 17/04* (2013.01); *C07C 17/06* (2013.01);
(Continued)

(58) Field of Classification Search
CPC ....... C07C 17/013; C07C 17/02; C07C 17/04; C07C 17/06; C07C 17/093; C07C 17/15;
(Continued)

(56) References Cited

U.S. PATENT DOCUMENTS 2,752,402 A 6/1956 Pye
2,792,342 A 5/1957 Tuwiner
(Continued)

FOREIGN PATENT DOCUMENTS

CA 1339833 C 4/1998
CN 1076735 A 9/1993
(Continued)

OTHER PUBLICATIONS

PCT/US2018/051636 International Search Report and Written Opinion dated Nov. 29, 2018.
(Continued)

*Primary Examiner* — Medhanit W Bahta
(74) *Attorney, Agent, or Firm* — Calera Corporation; Vandana Bansal

(57) ABSTRACT

There are provided methods and systems related to use of one or more lanthanide halides in an electrochemical oxidation of metal halide in anolyte where the metal ion is oxidized from lower oxidation state to higher oxidation state at an anode; and then further use of the one or more lanthanide halides and the metal halide with the metal ion in the higher oxidation state in a halogenation reaction of an unsaturated hydrocarbon or a saturated hydrocarbon to form one or more products comprising halohydrocarbon.

17 Claims, 3 Drawing Sheets

(51) Int. Cl.
  *C07C 17/04* (2006.01)
  *C07C 17/06* (2006.01)
  *C07C 17/093* (2006.01)
  *C07C 17/15* (2006.01)
  *C07C 17/152* (2006.01)
  *C07C 17/154* (2006.01)
  *C07C 17/156* (2006.01)
  *C07C 17/158* (2006.01)
  *C25B 9/10* (2006.01)
  *C25B 1/26* (2006.01)

(52) U.S. Cl.
  CPC .............. *C07C 17/093* (2013.01); *C25B 1/26* (2013.01); *C25B 9/10* (2013.01); *C07C 17/15* (2013.01); *C07C 17/152* (2013.01); *C07C 17/154* (2013.01); *C07C 17/156* (2013.01); *C07C 17/158* (2013.01)

(58) Field of Classification Search
  CPC ... C07C 17/152; C07C 17/154; C07C 17/156; C07C 17/158
  See application file for complete search history.

(56) References Cited

U.S. PATENT DOCUMENTS

| | | |
|---|---|---|
| 2,999,887 A | 9/1961 | Finlay et al. |
| 3,079,444 A | 2/1963 | Jacobowsky et al. |
| 3,214,481 A | 10/1965 | Heinemann et al. |
| 3,214,482 A | 10/1965 | Caropreso et al. |
| 3,427,235 A | 2/1969 | Le Duc |
| 3,437,712 A | 4/1969 | Long et al. |
| 3,461,180 A | 8/1969 | Heinemann et al. |
| 3,475,504 A | 10/1969 | Kircher et al. |
| 3,510,532 A | 5/1970 | Caropreso et al. |
| 3,607,420 A | 9/1971 | Cutler |
| 3,634,330 A | 1/1972 | Michel et al. |
| 3,635,803 A | 1/1972 | Binns et al. |
| 3,691,239 A | 9/1972 | Hackett et al. |
| 3,985,794 A | 10/1976 | Benedetto et al. |
| 4,056,452 A | 11/1977 | Campbell |
| 4,108,752 A | 8/1978 | Pohto et al. |
| 4,111,779 A | 9/1978 | Seko et al. |
| 4,190,508 A | 2/1980 | Kametani et al. |
| 4,256,719 A | 3/1981 | Van Andel |
| 4,269,678 A | 5/1981 | Faul et al. |
| 4,319,977 A | 3/1982 | Wortley |
| 4,324,625 A | 4/1982 | Cumbo |
| 4,376,019 A | 3/1983 | Gamlen et al. |
| 4,379,019 A | 4/1983 | Pool |
| 4,394,227 A | 7/1983 | Jaeger et al. |
| 4,402,811 A | 9/1983 | Klotz et al. |
| 4,409,076 A | 10/1983 | Seidel et al. |
| 4,538,011 A | 8/1985 | Drago et al. |
| 4,555,317 A | 11/1985 | Nicolas et al. |
| 4,581,116 A | 4/1986 | Plowman et al. |
| 4,595,469 A | 6/1986 | Foller |
| 4,643,818 A | 2/1987 | Seko et al. |
| 4,672,142 A | 6/1987 | Hundeck et al. |
| 4,726,887 A | 2/1988 | McIntyre |
| 4,767,519 A | 8/1988 | De Nora |
| 4,810,806 A | 3/1989 | Krespan |
| 4,814,420 A | 3/1989 | Brunelle et al. |
| 4,834,847 A | 5/1989 | McIntyre |
| 4,908,198 A | 3/1990 | Weinberg |
| 4,950,268 A | 8/1990 | Rink |
| 4,950,368 A | 8/1990 | Weinberg et al. |
| 5,050,603 A | 9/1991 | Stokes et al. |
| 5,296,107 A | 3/1994 | Harrison |
| 5,364,508 A | 11/1994 | Weres et al. |
| 5,437,771 A | 8/1995 | Shimamune et al. |
| 5,595,641 A | 1/1997 | Traini et al. |
| 5,891,318 A | 4/1999 | Freire et al. |
| 5,932,750 A | 8/1999 | Hayashi et al. |
| 6,117,286 A | 9/2000 | Shimamune et al. |
| 6,146,787 A | 11/2000 | Harrup et al. |
| 6,368,473 B1 | 4/2002 | Furuya et al. |
| 6,372,102 B1 | 4/2002 | Sakata et al. |
| 6,383,349 B1 | 5/2002 | Sakata et al. |
| 6,395,153 B1 | 5/2002 | Matousek et al. |
| 6,591,199 B2 | 7/2003 | Tremblay et al. |
| 7,404,878 B2 | 7/2008 | Katayama et al. |
| 7,569,083 B2 | 8/2009 | Katayama et al. |
| 7,616,006 B2 | 11/2009 | Tremblay et al. |
| 7,658,835 B2 | 2/2010 | Gestermann et al. |
| 7,708,867 B2 | 5/2010 | Yamada et al. |
| 7,735,274 B2 | 6/2010 | Constantz et al. |
| 7,744,761 B2 | 6/2010 | Constantz et al. |
| 7,749,476 B2 | 7/2010 | Constantz et al. |
| 7,753,618 B2 | 7/2010 | Constantz et al. |
| 7,754,169 B2 | 7/2010 | Constantz et al. |
| 7,771,684 B2 | 8/2010 | Constantz et al. |
| 7,790,012 B2 | 9/2010 | Kirk et al. |
| 7,797,137 B2 | 9/2010 | Veillette et al. |
| 7,815,880 B2 | 10/2010 | Constantz et al. |
| 7,818,276 B2 | 10/2010 | Veillette et al. |
| 7,829,053 B2 | 11/2010 | Constantz et al. |
| 7,837,842 B1 | 11/2010 | Mayers, Sr. et al. |
| 7,875,163 B2 | 1/2011 | Gilliam et al. |
| 7,887,694 B2 | 2/2011 | Constantz et al. |
| 7,906,028 B2 | 3/2011 | Constantz et al. |
| 7,914,652 B2 | 3/2011 | Yamada et al. |
| 7,914,685 B2 | 3/2011 | Constantz et al. |
| 7,922,809 B1 | 4/2011 | Constantz et al. |
| 7,931,809 B2 | 4/2011 | Constantz et al. |
| 7,933,511 B2 | 4/2011 | Masuki |
| 7,939,336 B2 | 5/2011 | Constantz et al. |
| 7,966,250 B2 | 6/2011 | Constantz et al. |
| 7,993,500 B2 | 8/2011 | Gilliam et al. |
| 7,993,511 B2 | 8/2011 | Gilliam et al. |
| 8,006,446 B2 | 8/2011 | Constantz et al. |
| 8,062,418 B2 | 11/2011 | Constantz et al. |
| 8,114,214 B2 | 2/2012 | Constantz et al. |
| 8,114,265 B2 | 2/2012 | Berriah et al. |
| 8,137,444 B2 | 3/2012 | Farsad et al. |
| 8,137,455 B1 | 3/2012 | Constantz et al. |
| 8,152,987 B2 | 4/2012 | Tremblay et al. |
| 8,177,909 B2 | 5/2012 | Constantz et al. |
| 8,197,649 B2 | 6/2012 | Saiki et al. |
| 8,221,957 B2 | 7/2012 | Iwai et al. |
| 8,333,944 B2 | 12/2012 | Constantz et al. |
| 8,357,270 B2 | 1/2013 | Gilliam et al. |
| 8,431,100 B2 | 4/2013 | Constantz et al. |
| 8,470,275 B2 | 6/2013 | Constantz et al. |
| 8,491,858 B2 | 7/2013 | Seeker et al. |
| 8,603,424 B2 | 12/2013 | Constantz et al. |
| 8,691,175 B2 | 4/2014 | Kendall et al. |
| 8,834,688 B2 | 9/2014 | Gilliam et al. |
| 8,857,118 B2 | 10/2014 | Constantz et al. |
| 8,869,477 B2 | 10/2014 | Ha et al. |
| 8,883,104 B2 | 11/2014 | Seeker et al. |
| 8,894,830 B2 | 11/2014 | Gilliam et al. |
| 8,906,156 B2 | 12/2014 | Constantz et al. |
| 8,932,400 B2 | 1/2015 | Chen et al. |
| 8,936,773 B2 | 1/2015 | Fernandez et al. |
| 8,940,139 B2 | 1/2015 | Asaumi et al. |
| 8,999,057 B2 | 4/2015 | Clodic et al. |
| 9,056,790 B2 | 6/2015 | Chen et al. |
| 9,061,940 B2 | 6/2015 | Chen et al. |
| 9,108,844 B2 | 8/2015 | Huss |
| 9,133,581 B2 | 9/2015 | Devenney et al. |
| 9,139,472 B2 | 9/2015 | Fernandez et al. |
| 9,175,410 B2 | 11/2015 | Izawa et al. |
| 9,181,624 B2 | 11/2015 | Sugiyama et al. |
| 9,187,834 B2 | 11/2015 | Albrecht et al. |
| 9,187,835 B2 | 11/2015 | Albrecht et al. |
| 9,200,375 B2 | 12/2015 | Gilliam et al. |
| 9,273,404 B2 | 3/2016 | Bulan et al. |
| 9,828,313 B2 | 11/2017 | Weiss et al. |
| 9,880,124 B2 | 1/2018 | Gilliam et al. |
| 9,957,621 B2 | 5/2018 | Albrecht et al. |
| 9,957,623 B2 | 5/2018 | Gilliam et al. |
| 1,016,105 A1 | 12/2018 | Gilliam et al. |

(56) References Cited

U.S. PATENT DOCUMENTS

| | | |
|---|---|---|
| 1,023,652 A1 | 3/2019 | Gilliam et al. |
| 1,028,722 A1 | 5/2019 | Weiss et al. |
| 2003/0150819 A1 | 8/2003 | Iseki et al. |
| 2004/0097767 A1 | 5/2004 | Gulotty et al. |
| 2004/0251199 A1 | 12/2004 | Benavides |
| 2004/0267063 A1 | 12/2004 | Harth et al. |
| 2005/0244689 A1 | 11/2005 | Horiguchi et al. |
| 2005/0283034 A1 | 12/2005 | Ganesan et al. |
| 2006/0124445 A1 | 6/2006 | Labrecque et al. |
| 2006/0149102 A1 | 7/2006 | Voight et al. |
| 2007/0014709 A1 | 1/2007 | Moyes et al. |
| 2007/0292762 A1 | 12/2007 | Johnson |
| 2008/0023339 A1 | 1/2008 | Berggren et al. |
| 2008/0029404 A1 | 2/2008 | Weber et al. |
| 2008/0223727 A1 | 9/2008 | Oloman et al. |
| 2008/0275279 A1 | 11/2008 | Podkolzin et al. |
| 2009/0001020 A1 | 1/2009 | Constantz et al. |
| 2009/0020044 A1 | 1/2009 | Constantz et al. |
| 2009/0029199 A1 | 1/2009 | Tao |
| 2009/0087698 A1 | 4/2009 | Huth et al. |
| 2009/0169452 A1 | 7/2009 | Constantz et al. |
| 2009/0202410 A1 | 8/2009 | Kawatra et al. |
| 2009/0301352 A1 | 12/2009 | Constantz et al. |
| 2009/0325031 A1 | 12/2009 | Sugawara et al. |
| 2010/0000444 A1 | 1/2010 | Constantz et al. |
| 2010/0024686 A1 | 2/2010 | Constantz et al. |
| 2010/0032347 A1 | 2/2010 | Ring et al. |
| 2010/0041927 A1 | 2/2010 | Olver et al. |
| 2010/0051469 A1 | 3/2010 | Stolberg |
| 2010/0051859 A1 | 3/2010 | House et al. |
| 2010/0063902 A1 | 3/2010 | Constantz et al. |
| 2010/0077691 A1 | 4/2010 | Constantz et al. |
| 2010/0077922 A1 | 4/2010 | Constantz et al. |
| 2010/0083880 A1 | 4/2010 | Constantz et al. |
| 2010/0084280 A1 | 4/2010 | Gilliam et al. |
| 2010/0108537 A1 | 5/2010 | Perego et al. |
| 2010/0111810 A1 | 5/2010 | Constantz et al. |
| 2010/0116683 A1 | 5/2010 | Gilliam et al. |
| 2010/0132556 A1 | 6/2010 | Constantz et al. |
| 2010/0132591 A1 | 6/2010 | Constantz et al. |
| 2010/0135865 A1 | 6/2010 | Constantz et al. |
| 2010/0135882 A1 | 6/2010 | Constantz et al. |
| 2010/0140103 A1 | 6/2010 | Gilliam et al. |
| 2010/0144521 A1 | 6/2010 | Constantz et al. |
| 2010/0150802 A1 | 6/2010 | Gilliam et al. |
| 2010/0154679 A1 | 6/2010 | Constantz et al. |
| 2010/0155258 A1 | 6/2010 | Kirk et al. |
| 2010/0158786 A1 | 6/2010 | Constantz et al. |
| 2010/0170805 A1 | 7/2010 | Krafft et al. |
| 2010/0179302 A1 | 7/2010 | Krafft et al. |
| 2010/0196104 A1 | 8/2010 | Constantz et al. |
| 2010/0200419 A1 | 8/2010 | Gilliam et al. |
| 2010/0219373 A1 | 9/2010 | Seeker et al. |
| 2010/0224503 A1 | 9/2010 | Kirk et al. |
| 2010/0229725 A1 | 9/2010 | Farsad et al. |
| 2010/0230293 A1 | 9/2010 | Gilliam et al. |
| 2010/0230830 A1 | 9/2010 | Farsad et al. |
| 2010/0236242 A1 | 9/2010 | Farsad et al. |
| 2010/0239467 A1 | 9/2010 | Constantz et al. |
| 2010/0239487 A1 | 9/2010 | Constantz et al. |
| 2010/0247410 A1 | 9/2010 | Constantz et al. |
| 2010/0258035 A1 | 10/2010 | Constantz et al. |
| 2010/0258450 A1 | 10/2010 | Burtch |
| 2010/0258506 A1 | 10/2010 | Berkowitz et al. |
| 2010/0270167 A1 | 10/2010 | McFarland |
| 2010/0276299 A1 | 11/2010 | Kelly et al. |
| 2010/0290967 A1 | 11/2010 | Detournay et al. |
| 2010/0313793 A1 | 12/2010 | Constantz et al. |
| 2010/0313794 A1 | 12/2010 | Constantz et al. |
| 2010/0319586 A1 | 12/2010 | Blount et al. |
| 2010/0326328 A1 | 12/2010 | Constantz et al. |
| 2011/0005938 A1 | 1/2011 | Wolf et al. |
| 2011/0028765 A1 | 2/2011 | Mehta |
| 2011/0030586 A1 | 2/2011 | Constantz et al. |
| 2011/0030957 A1 | 2/2011 | Constantz et al. |
| 2011/0033239 A1 | 2/2011 | Constantz et al. |
| 2011/0035154 A1 | 2/2011 | Kendall et al. |
| 2011/0036728 A1 | 2/2011 | Farsad |
| 2011/0042230 A1 | 2/2011 | Gilliam et al. |
| 2011/0054084 A1 | 3/2011 | Constantz et al. |
| 2011/0059000 A1 | 3/2011 | Constantz et al. |
| 2011/0067600 A1 | 3/2011 | Constantz et al. |
| 2011/0067603 A1 | 3/2011 | Constantz et al. |
| 2011/0067605 A1 | 3/2011 | Constantz et al. |
| 2011/0071309 A1 | 3/2011 | Constantz et al. |
| 2011/0076587 A1 | 3/2011 | Wang et al. |
| 2011/0079515 A1 | 4/2011 | Gilliam et al. |
| 2011/0081585 A1 | 4/2011 | Montgomery |
| 2011/0083968 A1 | 4/2011 | Gilliam et al. |
| 2011/0091366 A1 | 4/2011 | Kendall et al. |
| 2011/0091955 A1 | 4/2011 | Constantz et al. |
| 2011/0120888 A1 | 5/2011 | James et al. |
| 2011/0132234 A1 | 6/2011 | Constantz et al. |
| 2011/0135551 A1 | 6/2011 | House et al. |
| 2011/0147227 A1 | 6/2011 | Gilliam et al. |
| 2011/0152580 A1 | 6/2011 | Hook et al. |
| 2011/0203489 A1 | 8/2011 | Constantz et al. |
| 2011/0226989 A9 | 9/2011 | Seeker et al. |
| 2011/0240916 A1 | 10/2011 | Constantz et al. |
| 2011/0247336 A9 | 10/2011 | Farsad et al. |
| 2011/0269990 A1 | 11/2011 | Honda et al. |
| 2011/0277474 A1 | 11/2011 | Constantz et al. |
| 2011/0277670 A1 | 11/2011 | Self et al. |
| 2011/0297600 A1 | 12/2011 | Constantz et al. |
| 2011/0303551 A1 | 12/2011 | Gilliam et al. |
| 2011/0308964 A1 | 12/2011 | Gilliam et al. |
| 2011/0315561 A1 | 12/2011 | Rabaey et al. |
| 2012/0000789 A1 | 1/2012 | Turek et al. |
| 2012/0003125 A1 | 1/2012 | Madokoro et al. |
| 2012/0031303 A1 | 2/2012 | Constantz et al. |
| 2012/0111236 A1 | 5/2012 | Constantz et al. |
| 2012/0145047 A1 | 6/2012 | Constantz et al. |
| 2012/0152804 A1 | 6/2012 | Koseoglu et al. |
| 2012/0211421 A1 | 8/2012 | Self et al. |
| 2012/0213688 A1 | 8/2012 | Constantz et al. |
| 2012/0244053 A1 | 9/2012 | Self et al. |
| 2012/0275987 A1 | 11/2012 | Hiza et al. |
| 2012/0291675 A1 | 11/2012 | Camire et al. |
| 2012/0292196 A1 | 11/2012 | Albrecht et al. |
| 2012/0292197 A1 | 11/2012 | Albrecht et al. |
| 2012/0293110 A1 | 11/2012 | Frederick et al. |
| 2013/0034489 A1 | 2/2013 | Gilliam et al. |
| 2013/0206606 A1 | 8/2013 | Gilliam et al. |
| 2013/0240372 A1 | 9/2013 | Bulan et al. |
| 2013/0243674 A1 | 9/2013 | Constantz et al. |
| 2013/0256939 A1 | 10/2013 | Devenney et al. |
| 2014/0041553 A1 | 2/2014 | Constantz et al. |
| 2014/0332401 A1 | 11/2014 | Gilliam et al. |
| 2014/0353146 A1 | 12/2014 | Gilliam et al. |
| 2015/0000558 A1 | 1/2015 | Ha et al. |
| 2015/0031799 A1 | 1/2015 | Constantz et al. |
| 2015/0037231 A1 | 2/2015 | Seeker et al. |
| 2015/0038750 A1 | 2/2015 | Weiss et al. |
| 2015/0083607 A1 | 3/2015 | Gilliam et al. |
| 2015/0307400 A1 | 10/2015 | Devenney et al. |
| 2015/0307401 A1 | 10/2015 | Chen et al. |
| 2015/0337443 A1 | 11/2015 | Albrecht et al. |
| 2015/0353422 A1 | 12/2015 | Fernandez et al. |
| 2015/0361564 A1 | 12/2015 | Albrecht et al. |
| 2016/0040304 A1 | 2/2016 | Albrecht et al. |
| 2016/0060774 A1 | 3/2016 | Gilliam et al. |
| 2016/0076156 A1 | 3/2016 | Albrecht et al. |
| 2016/0108529 A1* | 4/2016 | Albrecht ............. C25B 1/00 526/344 |
| 2016/0230291 A1 | 8/2016 | Albrecht et al. |
| 2016/0273116 A1 | 9/2016 | Gilliam et al. |
| 2017/0073823 A1 | 3/2017 | Albrecht et al. |
| 2017/0121832 A1 | 5/2017 | Albrecht et al. |
| 2017/0250428 A1 | 8/2017 | Gilliam et al. |
| 2017/0309969 A1 | 10/2017 | Miller et al. |
| 2017/0342576 A1 | 11/2017 | McWaid et al. |
| 2018/0044267 A1 | 2/2018 | Weiss et al. |
| 2018/0216242 A1 | 8/2018 | Albrecht et al. |

(56) References Cited

U.S. PATENT DOCUMENTS

| | | | |
|---|---|---|---|
| 2018/0245223 | A1 | 8/2018 | Self et al. |
| 2018/0245226 | A1 | 8/2018 | Gilliam |
| 2019/0284708 | A1 | 9/2019 | Weiss et al. |

FOREIGN PATENT DOCUMENTS

| | | | |
|---|---|---|---|
| CN | 2530957 | Y | 1/2003 |
| CN | 101260530 | A | 9/2008 |
| CN | 102301037 | A | 12/2011 |
| CN | 102580492 | A | 7/2012 |
| CN | 102732910 | A | 10/2012 |
| CN | 103238233 | B | 9/2015 |
| EP | 0039547 | A1 | 11/1981 |
| EP | 0039547 | B1 | 7/1984 |
| EP | 0369732 | A1 | 5/1990 |
| EP | 1362133 | A1 | 11/2003 |
| EP | 2118004 | A1 | 11/2009 |
| EP | 2134664 | A1 | 12/2009 |
| EP | 2155350 | A2 | 2/2010 |
| EP | 2200732 | A1 | 6/2010 |
| EP | 2200948 | A1 | 6/2010 |
| EP | 2203067 | A1 | 7/2010 |
| EP | 2203241 | A1 | 7/2010 |
| EP | 2207753 | A1 | 7/2010 |
| EP | 2212033 | A1 | 8/2010 |
| EP | 2229341 | A1 | 9/2010 |
| EP | 2240257 | A1 | 10/2010 |
| EP | 2240629 | A1 | 10/2010 |
| EP | 2244808 | A1 | 11/2010 |
| EP | 2245215 | A1 | 11/2010 |
| EP | 2247366 | A1 | 11/2010 |
| EP | 2250127 | A1 | 11/2010 |
| EP | 2253600 | A1 | 11/2010 |
| EP | 2291550 | A1 | 3/2011 |
| EP | 2324528 | A1 | 5/2011 |
| EP | 2329875 | A1 | 6/2011 |
| EP | 2338136 | A1 | 6/2011 |
| EP | 1362133 | B1 | 7/2011 |
| EP | 2352574 | A1 | 8/2011 |
| EP | 2352706 | A1 | 8/2011 |
| EP | 2384520 | A1 | 11/2011 |
| EP | 2024062 | B1 | 2/2012 |
| EP | 2519483 | A1 | 11/2012 |
| EP | 2620207 | A2 | 7/2013 |
| EP | 2702009 | A2 | 3/2014 |
| EP | 2710650 | A1 | 3/2014 |
| EP | 2245214 | B1 | 10/2014 |
| EP | 2831120 | A1 | 2/2015 |
| EP | 2831313 | A1 | 2/2015 |
| EP | 2697410 | B1 | 6/2015 |
| FR | 1539499 | A | 9/1968 |
| GB | 812680 | A | 4/1959 |
| GB | 1019437 | A | 2/1966 |
| JP | 42-25045 | | 11/1942 |
| JP | S56169631 | A | 12/1981 |
| JP | S5727129 | A | 2/1982 |
| JP | S5874624 | A | 5/1983 |
| JP | S63293186 | A | 11/1988 |
| JP | H0238573 | B2 | 8/1990 |
| JP | H02290988 | A | 11/1990 |
| JP | H0356683 | A | 3/1991 |
| JP | H046290 | A | 1/1992 |
| JP | H0432594 | A | 2/1992 |
| JP | H05214573 | A | 8/1993 |
| JP | H105590 | A | 1/1998 |
| JP | H1081986 | A | 3/1998 |
| JP | H11256385 | A | 9/1999 |
| JP | 2000199093 | A | 7/2000 |
| JP | 2000355785 | A | 12/2000 |
| JP | 2001262387 | A | 9/2001 |
| JP | 2004027267 | A | 1/2004 |
| JP | 2005511670 | A | 4/2005 |
| JP | 2008546682 | A | 12/2008 |
| JP | 2009299111 | A | 12/2009 |
| MX | 2008005821 | A | 11/2009 |
| RU | 2222521 | C1 | 1/2004 |
| TW | 201313958 | A | 4/2013 |
| WO | WO-8002023 | A1 | 10/1980 |
| WO | WO-02094752 | A1 | 11/2002 |
| WO | WO-2004097073 | A1 | 11/2004 |
| WO | WO-2007058472 | A1 | 5/2007 |
| WO | WO-2008018928 | A2 | 2/2008 |
| WO | WO-2008148055 | A1 | 12/2008 |
| WO | WO-2009006295 | A2 | 1/2009 |
| WO | WO-2009086460 | A1 | 7/2009 |
| WO | WO-2009118162 | A1 | 10/2009 |
| WO | WO-2009146436 | A1 | 12/2009 |
| WO | WO-2009155378 | A1 | 12/2009 |
| WO | WO-2010006242 | A1 | 1/2010 |
| WO | WO-2010008896 | A1 | 1/2010 |
| WO | WO-2010009273 | A1 | 1/2010 |
| WO | WO-2010030826 | A1 | 3/2010 |
| WO | WO-2010039903 | A1 | 4/2010 |
| WO | WO-2010039909 | A1 | 4/2010 |
| WO | WO-2010048457 | A1 | 4/2010 |
| WO | WO-2010051458 | A1 | 5/2010 |
| WO | WO-2010055152 | A1 | 5/2010 |
| WO | WO-2010068924 | A1 | 6/2010 |
| WO | WO-2010074686 | A1 | 7/2010 |
| WO | WO-2010074687 | A1 | 7/2010 |
| WO | WO-2010087823 | A1 | 8/2010 |
| WO | WO-2010091029 | A1 | 8/2010 |
| WO | WO-2010093713 | A1 | 8/2010 |
| WO | WO-2010093716 | A1 | 8/2010 |
| WO | WO-2010101953 | A1 | 9/2010 |
| WO | WO-2010104989 | A1 | 9/2010 |
| WO | WO-2010132863 | A1 | 11/2010 |
| WO | WO-2010136744 | A1 | 12/2010 |
| WO | WO-2011008223 | A1 | 1/2011 |
| WO | WO-2011017609 | A1 | 2/2011 |
| WO | WO-2011038076 | A1 | 3/2011 |
| WO | WO-2011049996 | A1 | 4/2011 |
| WO | WO-2011066293 | A1 | 6/2011 |
| WO | WO-2011073621 | A1 | 6/2011 |
| WO | WO-2011075680 | A1 | 6/2011 |
| WO | WO-2011081681 | A1 | 7/2011 |
| WO | WO-2011097468 | A2 | 8/2011 |
| WO | WO-2011102868 | A1 | 8/2011 |
| WO | WO-2011116236 | A2 | 9/2011 |
| WO | WO-2012018434 | A1 | 2/2012 |
| WO | WO-2012149173 | A2 | 11/2012 |
| WO | WO-2012158969 | A1 | 11/2012 |
| WO | WO-2013019642 | A2 | 2/2013 |
| WO | WO-2013020066 | A2 | 2/2013 |
| WO | WO-2013049401 | A2 | 4/2013 |
| WO | WO-2013074252 | A1 | 5/2013 |
| WO | WO-2013077892 | A2 | 5/2013 |
| WO | WO-2013082811 | A1 | 6/2013 |
| WO | WO-2013148216 | A1 | 10/2013 |
| WO | WO-2013148279 | A1 | 10/2013 |
| WO | WO-2013165600 | A1 | 11/2013 |
| WO | WO-2015017585 | A1 | 2/2015 |
| WO | WO-2016044279 | A1 | 3/2016 |
| WO | WO-2016077368 | A1 | 5/2016 |
| WO | WO-2016149365 | A1 | 9/2016 |
| WO | WO-2017189680 | | 11/2017 |
| WO | WO-2017205676 | A1 | 11/2017 |
| WO | WO-2018156480 | | 8/2018 |
| WO | WO-2019060345 | A1 | 3/2019 |

OTHER PUBLICATIONS

Wikipedia "Cerium(III) chloride" Version: Jun. 28, 2017 (Jun. 28, 2017). Retrieved: Nov. 1, 2018 (Nov. 1, 2018) (https://en.wikipedia.org/w/index.php?title=Cerium(III)_chloride&oldid=787980857) p. 1, para 1.

EP16860934.5 Extended European Search Report dated May 9, 2019.

U.S. Appl. No. 14/460,697 Office Action dated Apr. 8, 2019.

U.S. Appl. No. 14/834,151 Office Action dated May 23, 2019.

U.S. Appl. No. 15/793,250 Notice of Allowance dated Feb. 25, 2019.

(56) References Cited

OTHER PUBLICATIONS

U.S. Appl. No. 15/935,442 Office Action dated Aug. 15, 2019.
U.S. Appl. No. 14/834,151 Office Action dated Sep. 26, 2019.
Zhao, et al. Electrochemistry of high concentration copper chloride complex. Anal. Chem. 2013; 85:7696-7703.
Acquah, et al. The electrochlorination of aliphatic hydrocarbons. J. Appl. Chem. Biotechnol. 1972; 22:1195-1200.
Andersson, et al. High power diode laser cladding. Fabricating and Metalworking. Mar. 2014; 24-26.
Benadda, B. et al. 1996. A study of Oxygen Absorption Kinetics in Ionic Cu(I) Aqueous Solutions. Chem. Eng. Technol. 19: 34-38.
Brugger, et al. Complexation of metal ions in brines: application of electronic spectroscopy in the study of the Cu(II)—LiCl—H2O system between 25 and 90° C. Geochimica et Cosmochimica Acta. 2001; 65(16):2691-2708.
Constantz, B. "The Risk of Implementing New Regulations on Game-Changing Technology: Sequestering CO2 in the Built Environment" AGU, Sep. 2009; 90(22), Jt. Assem, Suppl., Abstract.
European search report and opinion dated Feb. 25, 2015 for EP Application No. 12785945.2.
European search report and opinion dated May 11, 2015 for EP Application No. 13769321.4.
"European search report with opinion dated Dec. 8, 2016 for EP14832631.7".
"European search report with written opinion dated Feb. 17, 2017 for EP16188593.4".
European search report with written opinion dated Jul. 18, 2017 for EP17150726.
Friend, L. et al. 1974. Liquid-Phase Oxychlorination of Ethylene to Produce Vinyl Chloride. Homogeneous Catalysis. American Chemical Society. Piscataway, N.J. pp. 168-176.
Georgiadou, M. et al. 1998. Modelling of copper etching in aerated chloride solutions. Journal of Applied Electrochemistry. 28: 127-134.
Hine, F. et al. 1970. Mechanism of Oxidation of Cuprous Ion in Hydrochloric Acid Solution by Oxygen. Electrochimica Acta. 15: 769-781.
International search report and written opinion dated May 23, 2013 for PCT/US2013/031064.
International search report and written opinion dated Aug. 14, 2012 for PCT/US2012/038438.
International search report and written opinion dated Oct. 15, 2014 for PCT/US2014/048976.
International search report and written opinion dated Dec. 17, 2015 for PCT/US2015/050196.
Jhaveri, A.S., et al. 1967. Kinetics of absorption of oxygen in aqueous solutions of cuprous chloride. Chemical Engineering Science. 22: 1-6.
Kinoshita, et al. Mass-Transfer Study of Carbon Felt, Flow-Through Electrode. J. Electrochem. Soc. 1982; 129(9):1993-1997.
Kotora, et al. Selective Additions of Polyhalognated Compounds to Chloro Substituted Ethenes Catalyzed by a Copper Complex. React. Kinet. Catal. Lett. (no month, 1991), vol. 44, No. 2, pp. 415-419.
Krishnamoorthy, et al. Chlorination of substituted aromatics on graphite anode. Asian Journal of Chemistry. 2002; 14(3-4):1801-1803.
Langer, et al. Electrogenerative and Voltameiotic Processes. Ind. Eng. Chem. Process Des. Dev. 1979; 18(4):567-579.
Langer, et al. Electrogenerative Chlorination J. Electrochem. Soc. 1970; 117(4):510-511.
Liu, et al. A spectrophotometric study of aqueous copper(I)-chloride complexes in LiCl solutions between 100° C. and 250° C. Geochimica et Cosmochimica Acta. 2002; 66(20):3615-3633.
Logager, et al. Oxidation of Ferrous Ions by Ozone in Acidic Solutions. Inorg. Chem. 1992; 31:3523-3529.
Lundstrom, et al Redox potential characteristics of cupric chloride solutions. Hydrometallurgy. 2009; 95:285-289.

Margraf, et al. Copper(II) PMDTA and Copper(II) TMEDA Complexes: Precursors for the Synthesis of Dinuclear Copper(II) Complexes. Inorgancia Chimica Acta (no month, 2005), vol. 358, pp. 1193-1203.
Notice of allowance dated Feb. 12, 2018 for U.S. Appl. No. 15/341,260.
Notice of allowance dated Mar. 7, 2018 for U.S. Appl. No. 14/919,281.
Notice of allowance dated Mar. 16, 2018 for U.S. Appl. No. 14/855,262.
Notice of allowance dated Sep. 16, 2015 for U.S. Appl. No. 13/474,599.
Notice of allowance dated Sep. 28, 2017 for U.S. Appl. No. 14/446,791.
Notice of allowance dated Sep. 30, 2015 for U.S. Appl. No. 13/474,598.
Notice of allowance dated Oct. 9, 2015 for U.S. Appl. No. 13/799,131.
Office action dated Feb. 5, 2018 for U.S. Appl. No. 14/855,262.
Office action dated Feb. 8, 2018 for U.S. Appl. No. 14/834,151.
"Office action dated Feb. 9, 2017 for U.S. Appl. 14/446,791".
Office action dated Feb. 15, 2018 for U.S. Appl. No. 14/876,760.
Office action dated Mar. 2, 2018 for U.S. Appl. No. 14/814,935.
Office action dated Mar. 4, 2015 for U.S. Appl. No. 13/474,598.
Office action dated Mar. 8, 2018 for U.S. Appl. No. 15/341,260.
Office action dated Mar. 14, 2018 for U.S. Appl. No. 14/877,329.
Office action dated Mar. 21, 2018 for U.S. Appl. No. 14/879,525.
Office action dated Apr. 18, 2017 for U.S. Appl. 14/460,697.
Office action dated Apr. 23, 2015 for U.S. Appl. No. 13/474,599.
Office action dated May 14, 2018 for U.S. Appl. No. 14/834,151.
Office action dated May 16, 2018 for U.S. Appl. No. 14/460,697.
Office action dated Jun. 11, 2015 for U.S. Appl. No. 13/799,131.
Office Action dated Jun. 26, 2017 for U.S. Appl. No. 14/446,791.
Office action dated Jul. 9, 2015 for U.S. Appl. No. 13/474,598.
Office action dated Jul. 19, 2017 for U.S. Appl. No. 14/814,935.
Office action dated Aug. 6, 2015 for U.S. Appl. No. 13/474,598.
Office action dated Aug. 7, 2017 for U.S. Appl. No. 14/834,151.
Office action dated Aug. 8, 2017 for U.S. Appl. No. 14/814,935.
Office action dated Aug. 8, 2017 for U.S. Appl. No. 14/876,760.
Office action dated Aug. 10, 2017 for U.S. Appl. No. 14/460,697.
Office action dated Aug. 14, 2015 for U.S. Appl. No. 13/474,599.
Office action dated Aug. 22, 2017 for U.S. Appl. No. 15/341,260.
Office action dated Aug. 26, 2016 for U.S. Appl. No. 14/460,697.
Office action dated Aug. 27, 2015 for U.S. Appl. No. 13/474,598.
Office action dated Sep. 17, 2015 for U.S. Appl. No. 13/799,131.
Office action dated Oct. 19, 2016 for U.S. Appl. No. 14/446,791.
Office action dated Nov. 7, 2017 for U.S. Appl. No. 14/834,151.
Office action dated Nov. 16, 2017 for U.S. Appl. No. 14/814,935.
Office action dated Nov. 16, 2017 for U.S. Appl. No. 15/341,260.
Office action dated Nov. 27, 2017 for U.S. Appl. No. 14/876,760.
Office action dated Dec. 12, 2017 for U.S. Appl. No. 14/460,697.
"Office action dated Dec. 19, 2016 for U.S. Appl. 14/460,697".
Office action dated Dec. 21, 2017 for U.S. Appl. No. 14/919,281.
Powell, et al. Chemical speciation of environmentally significant metals with inorganic ligands. Pure Appl. Chem. 2007; 79(5):895-950.
Ralph, et al. Mass transport in an electrochemical laboratory filterpress reactor and its enhancement by turbulence promoters. Electrochemica Acta. 1996; 41(4):591-603.
Rollin, et al. The electrochemistry of nickel complexes with triphenylphosphine and ethylene in methylpyrrolidinone. Journal of Electroanalytical Chemistry and Interfacial Electrochemistry. 1985; 183(1-2):247-260.
Rorabacher. Electron transfer by copper centers. Chemical Centers. 2004; 104(2):651-698.
Spector, M.L. et al. 1967. Olefin Chlorination in Homogeneous Aqueous Copper Chloride Solutions. Industrial & Engineering Chemistry Process Design and Development. 6(3): 327-331.
U.S. Appl. No. 14/460,697 Office Action dated Oct. 9, 2018.
U.S. Appl. No. 14/814,935 Office Action dated Jul. 3, 2018.
U.S. Appl. No. 14/834,151 Office Action dated Oct. 17, 2018.
U.S. Appl. No. 15/338,235 Office Action dated Jun. 15, 2018.
U.S. Appl. No. 15/341,260 Office Action dated Jul. 23, 2018.
U.S. Appl. No. 15/793,250 Office Action dated Nov. 1, 2018.

(56) References Cited

OTHER PUBLICATIONS

Wikipedia definition of "Aqueous Solution". Accessed Jul. 29, 2015. 2 pages.
Wikipedia definition of "Solvent". Accessed Jul. 29, 2015. 14 pages.
Yuan, et al. Direct Electrochemical Synthesis and Crystal Structure of a Copper(II) Complex with a Chiral (S)-2-(diphenylmethanol-1-(2-pyridylmethyl)pyrrolidine. Inorganic Chemistry Communications (no month, 2005), vol. 8, pp. 1014-1017.

* cited by examiner

SYSTEMS AND METHODS USING LANTHANIDE HALIDE

CROSS-REFERENCE TO RELATED APPLICATIONS

This application claims benefit of U.S. Provisional Application No. 62/560,363, filed Sep. 19, 2017, which is incorporated herein by reference in its entirety in the present disclosure.

BACKGROUND

Halohydrocarbons are used commercially as solvents, pesticides, refrigerants, fire-resistant oils, ingredients of elastomers, adhesives and sealants, electrically insulating coatings, plasticizers, and plastics etc. Many halohydrocarbons have specialized uses in industry. For example, polyvinyl chloride, commonly known as PVC, may be made by polymerization of vinyl chloride monomer which in turn may be made from ethylene dichloride. PVC may be the third-most widely-produced plastic, after polyethylene and polypropylene. PVC is widely used in construction because it is durable, cheap, and easily worked.

The halohydrocarbons may be made by direct chlorination of hydrocarbons using chlorine gas. For example, ethylene dichloride may be made by direct chlorination of ethylene using chlorine gas made from the chlor-alkali process. The production of chlorine gas and caustic soda by electrolysis of aqueous solutions of sodium chloride or brine is one of the electrochemical processes demanding high-energy consumption. The total energy requirement is for instance about 2% in the USA and about 1% in Japan of the gross electric power generated, to maintain this process by the chlor-alkali industry. The high energy consumption may be related to high carbon dioxide emission owing to burning of fossil fuels. Therefore, there is a need for an economical and environmentally friendly process to make halohydrocarbons.

SUMMARY

In one aspect, there is provided a method, comprising: contacting an anode with an anode electrolyte wherein the anode electrolyte comprises metal halide, one or more lanthanide halides, and water; contacting cathode with a cathode electrolyte; applying voltage to the anode and the cathode and oxidizing the metal halide from a lower oxidation state to a higher oxidation state at the anode; and reacting an unsaturated hydrocarbon or a saturated hydrocarbon with the metal halide in the higher oxidation state and the one or more lanthanide halides in the anode electrolyte, to result in one or more products comprising halohydrocarbon. Subsequent to the reaction, the metal ion in the higher oxidation state in the metal halide is reduced to the lower oxidation state.

In one aspect, there is provided a method, comprising: contacting an anode with an anode electrolyte wherein the anode electrolyte comprises copper (I) chloride, copper (II) chloride, sodium chloride, cerium (III) chloride, and water; contacting cathode with a cathode electrolyte; applying voltage to the anode and the cathode and oxidizing the copper (I) chloride to copper (II) chloride at the anode; and reacting an unsaturated hydrocarbon or a saturated hydrocarbon with the copper (II) chloride and the cerium (III) chloride in the anode electrolyte, to result in one or more products comprising halohydrocarbon.

In one aspect, there is provided a system, comprising: an anode in contact with an anode electrolyte wherein the anode electrolyte comprises metal halide, one or more lanthanide halides, and water; and wherein the anode is configured to oxidize the metal halide from a lower oxidation state to a higher oxidation state; a cathode in contact with a cathode electrolyte; and a reactor operably connected to the anode chamber and configured to react the anode electrolyte comprising the metal halide in the higher oxidation state and the one or more lanthanide halides with an unsaturated hydrocarbon or saturated hydrocarbon to result in one or more products comprising halohydrocarbon.

In some embodiments of the aforementioned aspects, the lanthanide in the lanthanide halide is selected from the group consisting of lanthanum, cerium, praseodymium, neodymium, promethium, samarium, europium, gadolinium, terbium, dysprosium, holmium, erbium, thulium, ytterbium, lutetium, and combinations thereof.

In some embodiments of the aforementioned aspects and embodiments, the lanthanide halide is cerium halide and/or lanthanum halide.

In some embodiments of the aforementioned aspects and embodiments, the lanthanide in the lanthanide halide is cerium.

In some embodiments of the aforementioned aspects and embodiments, the lanthanide halide is cerium (III) halide.

In some embodiments of the aforementioned aspects and embodiments, the cerium halide is $CeCl_3.7H_2O$.

In some embodiments of the aforementioned aspects and embodiments, the one or more lanthanide halides, such as, but not limited to, cerium halide is in concentration range of between about 0.4-10 mol %.

In some embodiments of the aforementioned aspects and embodiments, the anode electrolyte further comprises salt. In some embodiments of the aforementioned embodiment, the salt comprises alkali metal halide or alkaline earth metal halide. In some embodiments of the aforementioned embodiments, the alkali metal halide is alkali metal chloride or alkaline earth metal halide is alkaline earth metal chloride. In some embodiments of the aforementioned embodiments, the alkali metal chloride comprises sodium chloride, potassium chloride, lithium chloride, or combinations thereof.

In some embodiments of the aforementioned aspects and embodiments, the anode electrolyte comprises the metal halide with metal ion in the higher oxidation state in range of about 4-17 mol %; the metal halide with metal ion in the lower oxidation state in range of about 0.5-5 mol %; the salt, such as an alkali metal halide, for example only, sodium chloride in range of about 0-10 mol %; and the lanthanide halide, for example only, cerium chloride in range of about 0.5-10 or 0.5-8 mol %.

In some embodiments of the aforementioned aspects and embodiments, ratio of the one or more lanthanide halides to the metal halide with metal ion in both lower oxidation state and higher oxidation state is between about 3:1 to 1:10.

In some embodiments of the aforementioned aspects and embodiments, ratio of the one or more lanthanide halides to the metal halide with metal ion in lower oxidation state is between about 10:1 to 1:10.

In some embodiments of the aforementioned aspects and embodiments, ratio of the one or more lanthanide halides to the alkali metal halide is between about 100:1 to 1:100.

In some embodiments of the aforementioned aspects and embodiments, ratio of the one or more lanthanide halides to sodium chloride is between about 100:1 to 1:100.

In some embodiments of the aforementioned aspects and embodiments, the one or more lanthanide halides results in more than 90% selectivity of the halohydrocarbon.

In some embodiments of the aforementioned aspects and embodiments, the one or more lanthanide halides reduce temperature of the reaction by more than 5° C. with substantially same or higher selectivity and/or space time yield (STY) of the halohydrocarbon as compared to when no lanthanide halide is used.

In some embodiments of the aforementioned aspects and embodiments, the one or more lanthanide halides improve economics and efficiency of the process as compared to when no lanthanide halide is used.

In some embodiments of the aforementioned aspects and embodiments, the metal halide is copper halide.

In some embodiments of the aforementioned aspects and embodiments, the metal halide in the lower oxidation state and the metal halide in the higher oxidation state is CuCl and $CuCl_2$, respectively.

In some embodiments of the aforementioned aspects and embodiments, the unsaturated hydrocarbon is a C2-C10 alkene or the saturated hydrocarbon is C2-C10 alkane.

In some embodiments of the aforementioned aspects and embodiments, the unsaturated hydrocarbon is ethylene, propylene, or butylene which reacts or is configured to react with the anode electrolyte comprising the metal halide in the higher oxidation state and the one or more lanthanide halides to form one or more products comprising ethylene dichloride, propylene dichloride or 1,4-dichlorobutane, respectively.

In some embodiments of the aforementioned aspects and embodiments, the unsaturated hydrocarbon is ethylene and the methods comprise reacting ethylene with the metal halide in the higher oxidation state, e.g. only $CuCl_2$ and the one or more lanthanide halides, e.g. only $CeCl_3$ in the anode electrolyte, to result in one or more products comprising EDC and chloroethanol (CE). In some embodiments, the method further comprise forming ethylene oxide from chloroethanol.

In some embodiments of the aforementioned aspects and embodiments, the unsaturated hydrocarbon is propylene and the methods comprise reacting propylene with the metal halide in the higher oxidation state, e.g. only $CuCl_2$ and the one or more lanthanide halides, e.g. only $CeCl_3$ in the anode electrolyte, to result in one or more products comprising propylene dichloride and propylene chlorohydrin (PCH). In some embodiments, the method further comprise forming propylene oxide from PCH.

In some embodiments of the aforementioned aspects and embodiments, the saturated hydrocarbon is methane, ethane, propane, or butane which reacts or is configured to react with the anode electrolyte comprising the metal halide in the higher oxidation state and the one or more lanthanide halides to form one or more products comprising dichloro methane, ethylene dichloride, propylene dichloride or 1,4-dichlorobutane, respectively.

In some embodiments of the aforementioned aspects and embodiments, the method further comprises forming an alkali, water, or hydrogen gas at the cathode or the system further comprises the cathode configured to form alkali, water, or hydrogen gas at the cathode.

In some embodiments of the aforementioned aspects and embodiments, the cathode electrolyte comprises water and the cathode is an oxygen depolarizing cathode that reduces or is configured to reduce oxygen and water to hydroxide ions; the cathode electrolyte comprises water and the cathode is a hydrogen gas producing cathode that reduces or is configured to reduce water to hydrogen gas and hydroxide ions; the cathode electrolyte comprises hydrochloric acid and the cathode is a hydrogen gas producing cathode that reduces or is configured to reduce hydrochloric acid to hydrogen gas; or the cathode electrolyte comprises hydrochloric acid and the cathode is an oxygen depolarizing cathode that reacts or is configured to react hydrochloric acid and oxygen gas to form water.

In some embodiments of the aforementioned aspects and embodiments, the metal ion in the metal halide is selected from the group consisting of iron, chromium, copper, tin, silver, cobalt, uranium, lead, mercury, vanadium, bismuth, titanium, ruthenium, osmium, europium, zinc, cadmium, gold, nickel, palladium, platinum, rhodium, iridium, manganese, technetium, rhenium, molybdenum, tungsten, niobium, tantalum, zirconium, hafnium, and combination thereof.

In some embodiments of the aforementioned aspects and embodiments, the metal ion in the metal halide is selected from the group consisting of iron, chromium, copper, and tin.

In some embodiments of the aforementioned aspects and embodiments, the metal ion in the metal halide is copper.

In some embodiments of the aforementioned aspects and embodiments, the lower oxidation state of metal ion in the metal halide is 1+, 2+, 3+, 4+, or 5+.

In some embodiments of the aforementioned aspects and embodiments, the higher oxidation state of metal ion in the metal halide is 2+, 3+, 4+, 5+, or 6+.

In some embodiments of the aforementioned aspects and embodiments, the metal ion in the metal halide is copper that is converted from $Cu^+$ to $Cu^{2+}$, metal ion in the metal halide is iron that is converted from $Fe^{2+}$ to $Fe^{3+}$, metal ion in the metal halide is tin that is converted from $Sn^{2+}$ to $Sn^{4+}$, metal ion in the metal halide is chromium that is converted from $Cr^{2+}$ to $Cr^{3+}$, metal ion in the metal halide is platinum that is converted from $Pt^{2+}$ to $Pt^{4+}$, or combination thereof.

In some embodiments of the aforementioned aspects and embodiments, the metal halide in the lower oxidation state is re-circulated back to the anode electrolyte.

BRIEF DESCRIPTION OF THE DRAWINGS

The novel features of the invention are set forth with particularity in the appended claims. A better understanding of the features and advantages of the present invention may be obtained by reference to the following detailed description that sets forth illustrative embodiments, in which the principles of the invention are utilized, and the accompanying drawings of which:

DETAILED DESCRIPTION

Figure 1:
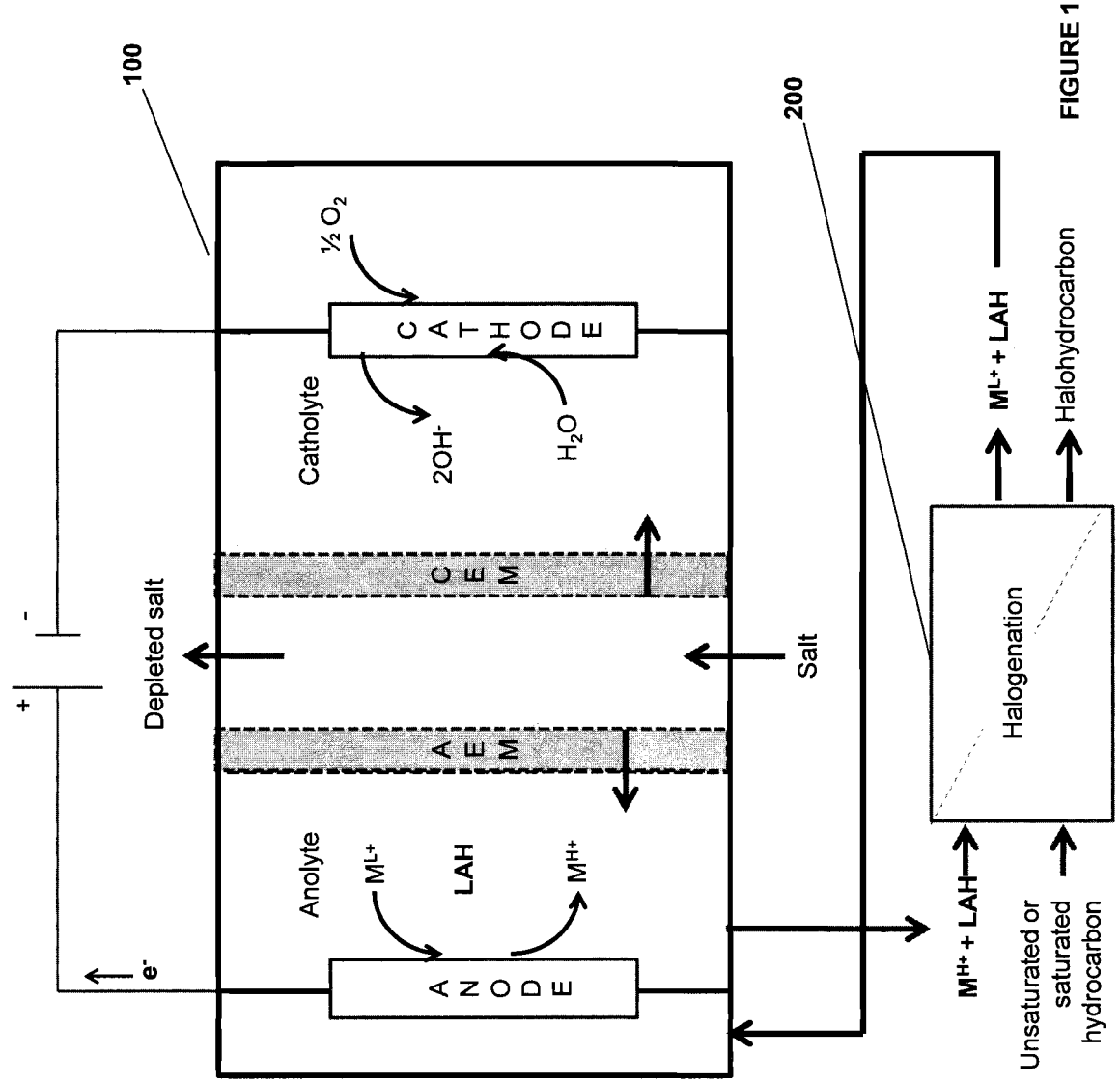
FIG. 1 is an illustration of some embodiments related to methods and systems comprising lanthanide halide.

Disclosed herein are systems and methods that relate to the use of one or more lanthanide halides in the electrochemical oxidation of the metal ion by the anode in the anode chamber where the metal ion is oxidized from the lower oxidation state to the higher oxidation state; and its further use in the halogenation of the unsaturated or saturated hydrocarbon.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges that are presented herein with numerical values may be construed as "about" numericals. The "about" is to provide literal support for the exact number that it precedes, as well as a number that is near to or approximately the number that the term precedes. In determining whether a number is near to or approximately a specifically recited number, the near or approximating unrequited number may be a number, which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a," "an," and "the" include plural references unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Compositions, Methods, and Systems

Provided herein are the methods, systems, and compositions related to the use of the one or more lanthanide halides in the electrochemical oxidation of the metal halide in the anolyte where the metal ion is oxidized from the lower oxidation state to the higher oxidation state at the anode; and then further use of the one or more lanthanide halides and the metal halide with the metal ion in the higher oxidation state in the halogenation reaction of the unsaturated hydrocarbon or a saturated hydrocarbon to form one or more products comprising halohydrocarbon.

Lanthanide Halide (LAH)

The "lanthanide halide" or "LAH" as used herein, includes halide of an element from lanthanide series. The element or the lanthanide from the lanthanide series is selected from the group consisting of lanthanum, cerium, praseodymium, neodymium, promethium, samarium, europium, gadolinium, terbium, dysprosium, holmium, erbium, thulium, ytterbium, lutetium, and combinations thereof. Chemically similar elements, scandium and yttrium, often collectively known as the rare earth elements, are also included in the lanthanide halides used herein. The lanthanide halide or LAH as used herein may be one lanthanide halide or may be a combination of two or more lanthanide halides, where the lanthanide in the one or more lanthanide halides is as noted above. The lanthanide halide can be in anhydrous form or in the form of a hydrate.

Applicants have discovered that the use of the one or more lanthanide halides significantly improve economics and efficiency of the electrochemical oxidation reaction as well as the halogenation reaction. It has been discovered that the use of the one or more lanthanide halides provide several advantages including but not limited to, improving the operation parameters such as solubility of the metal halide, conversion per pass, reaction temperature, reaction pressure, residence time of the reaction mixture, water removal, and/or optimizing the anolyte composition; to achieve performance parameters, such as but not limited to, higher selectivity of the halohydrocarbon, higher space time yield (STY) of the halohydrocarbon, and/or lower electrochemical cell voltage.

Typically, solubility of the anolyte may be driven by the anolyte composition (including but not limited to, concentration of the metal halide (both in lower oxidation state and higher oxidation state of the metal), concentration of the one or more lanthanide halides, other salt if any, water, etc.) and/or temperature. The use of membranes may limit the temperature in the electrochemical cell. Water removal and water addition may be possible at multiple points of the recycling anolyte but active water removal may be energy intensive and may negatively affect the energy balance of the system. The compositions may be limited to ratios that allow solubility at the lowest temperature point. Therefore, the solubility of the anolyte may limit the range of the concentrations of the metal halide, the concentrations of the one or more lanthanide halides, and optionally the concentration of the salt in the anolyte composition.

Meanwhile, the selectivity of the halohydrocarbon product may be affected by the operation parameters such as, temperature and/or the anolyte composition. The voltage of the electrochemical cell may also depend on anolyte composition as well. For example, high salt concentrations/low water content may lead to higher selectivity of the one or more products albeit higher voltages and lower solubilities in the electrochemical cell. The higher voltage and lower solubility may both drive operation cost of the system, therefore, the need to optimize the anolyte composition to high selectivity and low voltage is desired. For example only, an increase in the concentration of the metal halide with metal ion in the higher oxidation state, e.g. only, $CuCl_2$ while keeping the other salt concentrations constant (and in the absence of the lanthanide halide) may lead to an increased STY and selectivity of the halohydrocarbon product, e.g. ethylene dichloride, but at the same time may decrease anolyte solubility and increase the electrochemical voltage.

The addition of the one or more lanthanide halides to the anolyte composition improves one or more of the operation parameters' window such as, but not limited to, optimizes the concentration range of the anolyte composition, the solubility of the metal halide, conversion per pass, reaction temperature, reaction pressure, residence time of the reaction mixture, and/or water removal, etc.; to achieve performance parameters, such as but not limited to, high selectivity of the halohydrocarbon, high space time yield (STY) of the halohydrocarbon, and/or low electrochemical voltage (further shown in the examples). In some embodiments, the one or more lanthanide halides improve economics and efficiency of the process as compared to when no lanthanide halide is used.

In one aspect, there are provided methods comprising contacting an anode with an anode electrolyte wherein the anode electrolyte comprises metal halide, one or more lanthanide halides, and water; contacting cathode with a cathode electrolyte; applying voltage to the anode and the cathode and oxidizing the metal halide from a lower oxidation state to a higher oxidation state at the anode; and reacting an unsaturated hydrocarbon or a saturated hydrocarbon with the metal halide in the higher oxidation state and the one or more lanthanide halides in the anode electrolyte, to result in one or more products comprising halohydrocarbon.

In one aspect, there is provided a system, comprising an anode in contact with an anode electrolyte wherein the anode electrolyte comprises metal halide, one or more lanthanide halides, and water; and wherein the anode is configured to oxidize the metal halide from a lower oxidation state to a higher oxidation state; a cathode in contact with a cathode electrolyte; and a reactor operably connected to the anode chamber and configured to react the anode electrolyte comprising the metal halide in the higher oxidation state and the one or more lanthanide halides with an unsaturated hydrocarbon or saturated hydrocarbon to result in one or more products comprising halohydrocarbon.

Some embodiments of the methods and systems are as illustrated in FIG. 1. As shown in FIG. 1, the electrochemical system 100 includes an anode chamber with an anode in contact with an anode electrolyte or anolyte where the anolyte contains metal halide with metal ions in lower oxidation state (represented as $M^{L+}$) which are converted by the anode to metal halide with metal ions in higher oxidation state (represented as $M^{H+}$). The lanthanide halide is shown as LAH in the anode electrolyte. It is to be understood that the LAH includes one lanthanide halide or a combination of two or more lanthanide halides. The lanthanide halides have been described herein. As used herein "lower oxidation state" represented as L+ in $M^{L+}$ includes the lower oxidation state of the metal. For example, lower oxidation state of the metal ion may be 1+, 2+, 3+, 4+, or 5+. As used herein "higher oxidation state" represented as H+ in $M^{H+}$ includes the higher oxidation state of the metal. For example, higher oxidation state of the metal ion may be 2+, 3+, 4+, 5+, or 6+. In some embodiments, the anode does not use or form a gas.

The electron(s) generated at the anode are used to drive the reaction at the cathode. The cathode reaction may be any reaction known in the art. The anode chamber and the cathode chamber may be separated by one ion exchange membrane (IEM) that may allow the passage of ions, such as, but not limited to, sodium ions in some embodiments to the cathode electrolyte if the anode electrolyte is sodium chloride. In some embodiments, the ion exchange membrane allows the passage of anions, such as, but not limited to, halide ions to the anode electrolyte if the cathode electrolyte is e.g., sodium chloride, sodium bromide, sodium iodide, or an equivalent solution. In some embodiments, the ion exchange membrane is a cation exchange membrane (CEM), an anion exchange membrane (AEM); or combination thereof. In some embodiments, the electrochemical systems of the invention include two ion exchange membranes. As shown in FIG. 1, the anode and the cathode chamber may be separated by two IEMs, the AEM and the CEM. A third electrolyte (e.g., sodium chloride, sodium bromide, sodium iodide, or an equivalent salt solution described herein) is disposed between the AEM and the CEM. The cations, such as alkali metal or alkaline earth metal cations from the third electrolyte pass through CEM to form corresponding hydroxide in the cathode chamber and the halide anions such as, chloride, bromide or iodide ions, from the third electrolyte pass through the AEM to form metal halide in the anode chamber. The third electrolyte, after the transfer of the ions, can be withdrawn from the middle chamber as depleted ion solution. For example, in some embodiments when the third electrolyte is sodium chloride solution, then after the transfer of the sodium ions to the cathode electrolyte and transfer of chloride ions to the anode electrolyte, the depleted sodium chloride solution may be withdrawn from the middle chamber. The depleted salt solution may be used for commercial purposes or may be transferred to the anode and/or cathode chamber as an electrolyte or concentrated for re-use as the third electrolyte. In some embodiments, the depleted salt solution may be useful for preparing desalinated water. Examples of IEMs have been described herein.

Some reactions that may occur at the cathode include, but not limited to, reaction of water to form hydroxide ions and hydrogen gas; reaction of oxygen gas and water to form hydroxide ions; reduction of HCl to form hydrogen gas; or reaction of HCl and oxygen gas to form water. It is to be understood that the hydroxide forming cathode, as illustrated in FIG. 1 is for illustration purposes only and other cathodes such as, cathode reducing HCl to form hydrogen gas or cathode reacting both HCl and oxygen gas to form water, are equally applicable to the systems. Such cathodes have been described herein.

The anode electrolyte comprising the metal halide with metal ions in the higher oxidation state and LAH is then delivered to system 200 for reaction with the unsaturated or saturated hydrocarbon to generate one or more products comprising halohydrocarbon. The halohydrocarbons, other side products, and the products further generated from the halohydrocarbons have been described herein. The metal ion in the metal halide is reduced to the lower oxidation state. The anode electrolyte comprising the metal halide with the metal ion in the lower oxidation state and the LAH is then re-circulated back to the anode chamber.

Figure 2:
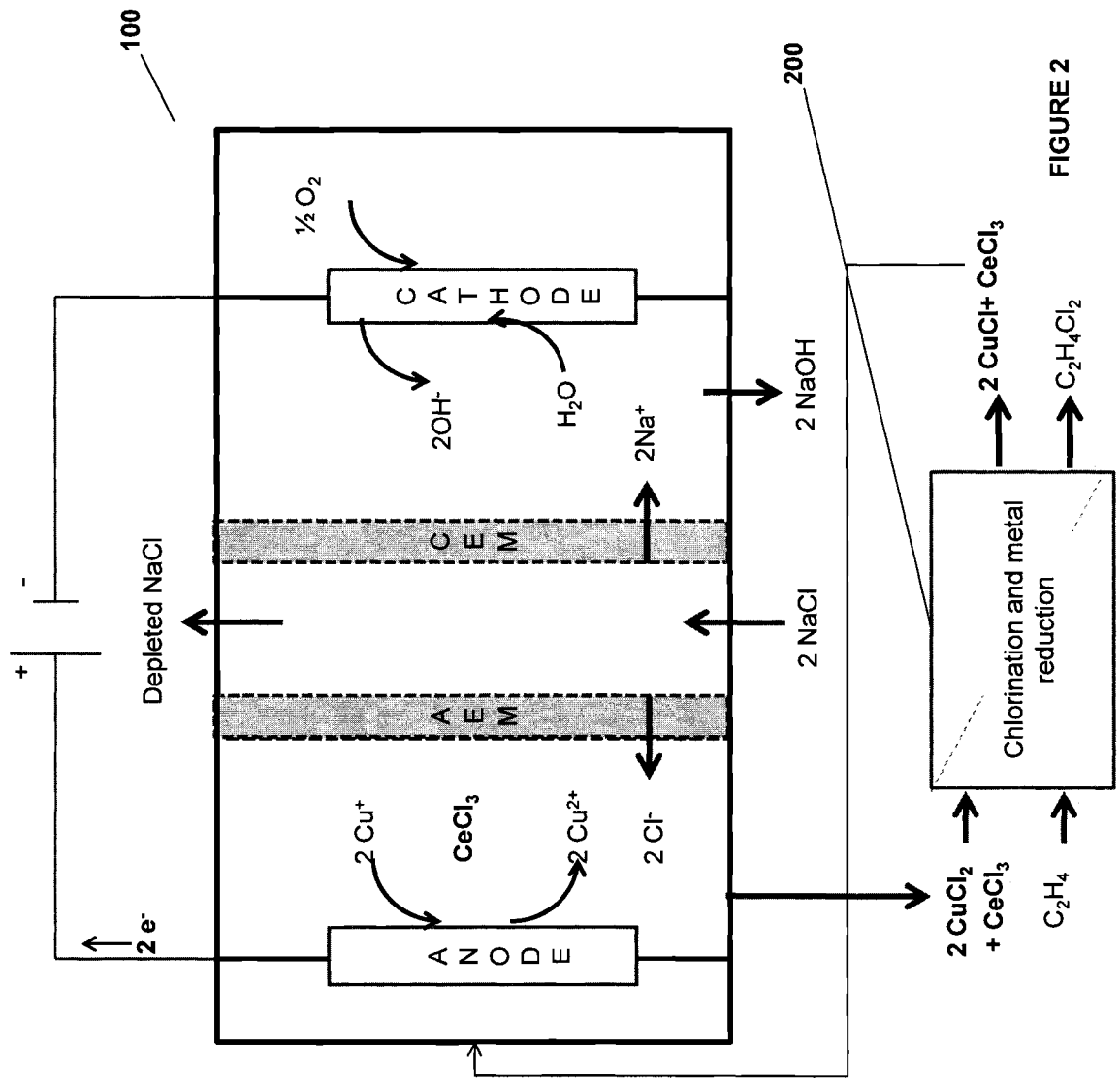
FIG. 2 is an illustration of some embodiments related to methods and systems comprising lanthanide halide.

An example of the system of FIG. 1 is illustrated in FIG. 2. The electrochemical system 100 of FIG. 2 has an anolyte comprising CuCl (copper (I) chloride) as an example of the metal halide with metal ion in the lower oxidation state; $CeCl_3$ as an example of LAH; NaCl as an example of salt such as an alkali metal chloride; and $CuCl_2$ (copper (II) chloride) as an example of the metal halide with metal ion in the higher oxidation state in water. CuCl gets oxidized to $CuCl_2$ at the anode in the presence of $CeCl_3$. The salt fed to the middle chamber provides Cl⁻ to the anode electrolyte where the $Cu^{2+}$ ions combine with chloride ions to form $CuCl_2$. The anode electrolyte containing metal chloride CuCl, $CuCl_2$, $CeCl_3$, and NaCl in water can be then reacted with the unsaturated hydrocarbon, such as, but not limited to, ethylene to undergo reduction of the metal ion to the lower oxidation state to form CuCl and form dichlorohydrocarbon, such as, but not limited to, ethylene dichloride. The CuCl, $CeCl_3$, and NaCl in water are then re-circulated back to the anode chamber for conversion to $CuCl_2$.

It is to be understood that the system of FIGS. 1 and 2 is for illustration purposes only and other metal ions with different oxidations states; LAH other than cerium chloride or combination of cerium chloride with other lanthanide halides; other unsaturated or saturated hydrocarbons; other products; other halohydrocarbons; and other electrochemical systems forming products at the cathode other than alkali, such as water or hydrogen gas in the cathode chamber, are equally applicable to the system. Various examples of the metal halides, the LAHs, the unsaturated or the saturated hydrocarbon, the salt, the halohydrocarbons, and other reactions at the cathode, have been described herein and all are within the scope of the invention. Any of the combinations of the metal halides, the LAHs, the unsaturated or the saturated hydrocarbon, the salt, the halohydrocarbons, and other reactions at the cathode are well within the scope of the invention.

In some embodiments of the aforementioned aspects, the lanthanide in the lanthanide halide or LAH is selected from the group consisting of lanthanum, cerium, praseodymium, neodymium, promethium, samarium, europium, gadolinium, terbium, dysprosium, holmium, erbium, thulium, ytterbium, lutetium, and combinations thereof. In some embodiments of the aforementioned aspects, the lanthanide in the lanthanide halide or LAH is selected from the group consisting of lanthanum, cerium, praseodymium, neodymium, promethium, samarium, gadolinium, terbium, dysprosium, holmium, erbium, thulium, ytterbium, lutetium, and combinations thereof. In some embodiments of the aforementioned aspects and embodiments, the lanthanide in the lanthanide halide is selected from the group consisting of lanthanum, cerium, praseodymium, neodymium, promethium, samarium, and combinations thereof. In some embodiments of the aforementioned aspects and embodiments, the lanthanide in the lanthanide halide is selected from the group consisting of lanthanum, cerium, terbium, dysprosium, holmium, erbium, thulium, ytterbium, lutetium, and combinations thereof. In some embodiments of the aforementioned aspects and embodiments, the lanthanide halide is cerium halide and/or lanthanum halide.

The "halide" as used herein, includes chloride, bromide, iodide or fluoride.

In some embodiments of the aforementioned aspects and embodiments, the lanthanide halide is cerium halide. In some embodiments of the aforementioned aspects and embodiments, the lanthanide halide is cerium (III) halide. In some embodiments of the aforementioned aspects and embodiments, the cerium halide is $CeCl_3.7H_2O$ or any other hydrate.

In some embodiments of the aforementioned aspects and embodiments, the lanthanide halide is lanthanum halide. In some embodiments of the aforementioned aspects and embodiments, the lanthanum halide is lanthanum (III) halide. In some embodiments of the aforementioned aspects and embodiments, the lanthanum halide is $LaCl_3.7H_2O$ or any other hydrate.

In some embodiments of the aforementioned aspects and embodiments, the one or more lanthanide halides, for example only, the cerium halide in the methods and systems provided herein, is in concentration range of between about 0.4-10 mol %; or between about 0.4-8 mol %; or between about 0.4-7 mol %; or between about 0.4-6 mol %; or between about 0.4-5 mol %; or between about 0.4-4 mol %; or between about 0.4-3 mol %; or between about 0.4-2 mol %; or between about 0.4-1 mol %; or between about 1-10 mol %; or between about 1-8 mol %; or between about 1-6 mol %; or between about 1-5 mol %; or between about 1-4 mol %; or between about 1-2 mol %; or between about 2-10 mol %; or between about 2-5 mol %; or between about 4-10 mol %; or between about 4-8 mol %; or between about 5-10 mol %; or between about 5-8 mol %; or between about 6-10 mol %; or between about 7-10 mol %; or between about 8-10 mol %.

In some embodiments of the aforementioned aspects and embodiments, the anode electrolyte further comprises salt. "Salt" as used herein includes a compound that adds salinity to water. In some embodiments of the aforementioned embodiment, the salt comprises alkali metal halide and/or alkaline earth metal halide. In some embodiments of the aforementioned embodiments, the alkali metal halide is alkali metal chloride or alkaline earth metal halide is alkaline earth metal chloride. In some embodiments of the aforementioned embodiments, the alkali metal chloride comprises sodium chloride, potassium chloride, lithium chloride, or the like. In some embodiments of the aforementioned embodiments, the alkaline earth metal chloride comprises beryllium chloride, magnesium chloride, calcium chloride, strontium chloride, barium chloride, or the like.

In some embodiments of the aforementioned aspects and embodiments, the anode electrolyte comprises the metal halide with metal ion in the higher oxidation state in range of about 4-17 mol %; and the metal halide with metal ion in the lower oxidation state in range of about 0.5-5 mol %.

In some embodiments of the aforementioned aspects and embodiments, the anode electrolyte comprises the metal halide with metal ion in the higher oxidation state in range of about 4-17 mol %; the metal halide with metal ion in the lower oxidation state in range of about 0.5-5 mol %; and the one or more lanthanide halides in range of about 0.5-10 mol %.

In some embodiments of the aforementioned aspects and embodiments, the anode electrolyte comprises the metal halide with metal ion in the higher oxidation state in range of about 4-17 mol %; the metal halide with metal ion in the lower oxidation state in range of about 0.5-5 mol %; the salt in range of about 0-10 mol %; and the one or more lanthanide halides in range of about 0.5-10 mol %.

In some embodiments of the aforementioned aspects and embodiments, the anode electrolyte comprises the metal halide with metal ion in the higher oxidation state in range of about 4-17 mol %; the metal halide with metal ion in the lower oxidation state in range of about 0.5-5 mol %; the alkali metal halide or alkaline earth metal halide in range of about 0-10 mol %; and the one or more lanthanide halides in range of about 0.5-10 mol %.

In some embodiments of the aforementioned aspects and embodiments, the anode electrolyte comprises $CuCl_2$ in range of about 4-17 mol %; CuCl in range of about 0.5-5 mol %; sodium chloride in range of about 0-10 mol %; and cerium chloride in range of about 0.5-10 mol %.

In some embodiments of the aforementioned aspects and embodiments, the anode electrolyte comprises $CuCl_2$ in range of about 4-17 mol %; CuCl in range of about 0.5-5 mol %; sodium chloride in range of about 0-10 mol %; and $CeCl_3.7H_2O$ in range of about 0.5-10 mol %.

In the above noted aspects and embodiments, the anode electrolyte comprises water. In the above noted aspects and embodiments, the anode electrolyte comprises water in remaining mol %.

In some embodiments of the aforementioned aspects and embodiments, ratio of the one or more lanthanide halides to the metal halide with metal ion in both lower oxidation state and higher oxidation state is between about 3:1 to 1:10; or about 2:1 to 1:5.

In some embodiments of the aforementioned aspects and embodiments, ratio of the one or more lanthanide halides to the metal halide with metal ion in lower oxidation state is between about 10:1 to 1:10; or between about 5:1 to 1:5.

In some embodiments of the aforementioned aspects and embodiments, ratio of the one or more lanthanide halides to the alkali metal halide is between about 100:1 to 1:100; or between about 50:1 to 1:50; or between about 10:1 to 1:10.

In some embodiments of the aforementioned aspects and embodiments, ratio of the one or more lanthanide halides to sodium chloride is between about 100:1 to 1:100; or between about 50:1 to 1:50; or between about 10:1 to 1:10.

In some embodiments of the aforementioned aspects and embodiments, the one or more lanthanide halides result in more than 90% or more than 95% selectivity of the halohydrocarbon.

In some embodiments of the aforementioned aspects and embodiments, the one or more lanthanide halides reduce temperature of the reaction by more than 5° C. or more than 10° C. with substantially same or higher selectivity and/or space time yield (STY) of the halohydrocarbon as compared to when no lanthanide halide is used. In some embodiments of the aforementioned aspects and embodiments, the one or more lanthanide halides improve economics and efficiency of the process as compared to when no lanthanide halide is used.

In all the above noted aspects, the lanthanide in the one or more lanthanide halides is any one of the lanthanide described herein.

Provided below is the detailed description of the electrochemical systems and methods and its components; and halogenation reaction systems and methods and its components.

Electrochemical Methods and Systems

The electrochemical cell may be any electrochemical cell where the metal ion in the lower oxidation state is converted to the metal ion in the higher oxidation state in the anolyte in the anode chamber in the presence of one or more lanthanide halides. An example of the electrochemical cell is illustrated in FIGS. 1 and 2. In the electrochemical cell, cathode reaction may be any reaction that does or does not form an alkali in the cathode chamber. Such cathode consumes electrons and carries out any reaction including, but not limited to, the reaction of water to form hydroxide ions and hydrogen gas; or reaction of oxygen gas and water to form hydroxide ions; or reduction of protons from an acid such as hydrochloric acid to form hydrogen gas; or reaction of protons from hydrochloric acid and oxygen gas to form water.

In some embodiments, the electrochemical cells may include production of an alkali in the cathode chamber of the cell. The alkali generated in the cathode chamber may be used as is for commercial purposes or may be treated with divalent cations to form divalent cation containing carbonates/bicarbonates. In some embodiments, the alkali generated in the cathode chamber may be used to sequester or capture carbon dioxide. The carbon dioxide may be present in flue gas emitted by various industrial plants. The carbon dioxide may be sequestered in the form of carbonate and/or bicarbonate products. In some embodiments, the metal compound with metal in the higher oxidation state may be withdrawn from the anode chamber and is used for any commercial process that is known to skilled artisan in the art. Therefore, both the anode electrolyte as well as the cathode electrolyte can be used for generating products that may be used for commercial purposes thereby providing a more economical, efficient, and less energy intensive process.

In some embodiments, the metal compound produced by the anode chamber may be used as is or may be purified before reacting with the unsaturated hydrocarbon or saturated hydrocarbon for the generation of the one or more products comprising halohydrocarbon. In some embodiments, the metal compound may be used on-site where the unsaturated hydrocarbon or saturated hydrocarbon is generated and/or in some embodiments, the metal compound and the one or more lanthanide halides withdrawn from the anode chamber may be transferred to a site where the unsaturated hydrocarbon or saturated hydrocarbon is generated and the halohydrocarbon may be formed from it. In some embodiments, the metal compound may be formed in the electrochemical system and used on-site where the unsaturated hydrocarbon such as, but not limited to, ethylene gas is generated or transferred to and/or in some embodiments, the metal compound and the one or more lanthanide halides in the anolyte withdrawn from the anode chamber may be transferred to a site where the unsaturated hydrocarbon such as, but not limited to, ethylene gas is generated or transferred to and halohydrocarbon, e.g., chlorohydrocarbon is formed from it. In some embodiments, the ethylene gas generating facility is integrated with the electrochemical system to simultaneously produce the metal compound in the higher oxidation state and the ethylene gas and treat them with each other to form a product, such as ethylene dichloride (EDC). In some embodiments, the electrochemical system of the invention is integrated with vinyl chloride monomer (VCM) production facility or polyvinylchloride (PVC) production facility such that the EDC formed via the systems and methods of the invention is used in VCM and/or PVC production.

In some embodiments, the electrochemical methods and systems do not produce chlorine gas at the anode. In some embodiments, the methods and systems do not require chlorine gas for the halogenation of unsaturated or saturated hydrocarbons.

Metal Halide

The "metal ion" or "metal" as used herein, includes any metal ion in the metal halide capable of being converted from lower oxidation state to higher oxidation state. Examples of metal ions include, but not limited to, iron, chromium, copper, tin, silver, cobalt, uranium, lead, mercury, vanadium, bismuth, titanium, ruthenium, osmium, zinc, cadmium, gold, nickel, palladium, platinum, rhodium, iridium, manganese, technetium, rhenium, molybdenum, tungsten, niobium, tantalum, zirconium, hafnium, and combination thereof. In some embodiments, the metal ions include, but not limited to, iron, copper, tin, chromium, or combination thereof. In some embodiments, the metal ion is copper. In some embodiments, the metal ion is tin. In some embodiments, the metal ion is iron. In some embodiments, the metal ion is chromium. In some embodiments, the metal ion is platinum. The "oxidation state" as used herein, includes degree of oxidation of an atom in a substance. For example, in some embodiments, the oxidation state is the net charge on the ion. Some examples of the reaction of the metal ions at the anode are as shown in Table I below (SHE is standard hydrogen electrode). The theoretical values of the anode potential are also shown. It is to be understood that some variation from these voltages may occur depending on conditions, pH, concentrations of the electrolytes, etc and such variations are well within the scope of the invention.

TABLE I

| Anode Reaction | Anode Potential (V vs. SHE) |
|---|---|
| $Ag^+ \rightarrow Ag^{2+} + e^-$ | −1.98 |
| $Co^{2+} \rightarrow Co^{3+} + e^-$ | −1.82 |
| $Pb^{2+} \rightarrow Pb^{4+} + 2e^-$ | −1.69 |
| $Ce^{3+} \rightarrow Ce^{4+} + e^-$ | −1.44 |
| $2Cr^{3+} + 7H_2O \rightarrow Cr_2O_7^{2-} + 14H^+ + 6e^-$ | −1.33 |
| $Tl^+ \rightarrow Tl^{3+} + 2e^-$ | −1.25 |
| $Hg_2^{2+} \rightarrow 2Hg^{2+} + 2e^-$ | −0.91 |
| $Fe^{2+} \rightarrow Fe^{3+} + e^-$ | −0.77 |
| $V^{3+} + H_2O \rightarrow VO^{2+} + 2H^+ + e^-$ | −0.34 |
| $U^{4+} + 2H_2O \rightarrow UO_2^{2+} + 4H^+ + e^-$ | −0.27 |
| $Bi^+ \rightarrow Bi^{3+} + 2e^-$ | −0.20 |
| $Tl^{3+} + H_2O \rightarrow TlO^{2+} + 2H^+ + e^-$ | −0.19 |
| $Cu^+ \rightarrow Cu^{2+} + e^-$ | −0.16 |
| $UO_2^+ \rightarrow UO_2^{2+} + e^-$ | −0.16 |
| $Sn^{2+} \rightarrow Sn^{4+} + 2e^-$ | −0.15 |
| $Ru(NH_3)_6^{2+} \rightarrow Ru(NH_3)_6^{3+} + e^-$ | −0.10 |
| $V^{2+} \rightarrow V^{3+} + e^-$ | +0.26 |
| $Eu^{2+} \rightarrow Eu^{3+} + e^-$ | +0.35 |
| $Cr^{2+} \rightarrow Cr^{3+} + e^-$ | +0.42 |
| $U^{3+} \rightarrow U^{4+} + e^-$ | +0.52 |

The metal ion may be present as a compound of the metal or an alloy of the metal or combination thereof. In some embodiments, the anion attached to the metal is same as the anion of the electrolyte. For example, for sodium or potassium chloride used as an electrolyte, a metal chloride, such as, but not limited to, iron chloride, copper chloride, tin chloride, chromium chloride etc. is used as the metal compound. For example, for sodium or potassium bromide used as an electrolyte, a metal bromide, such as, but not limited to, iron bromide, copper bromide, tin bromide etc. is used as the metal compound.

In some embodiments, the anion of the electrolyte may be partially or fully different from the anion of the metal. In some embodiments, the anode electrolyte may be a combination of ions similar to the metal anion and anions different from the metal ion. For example, the anode electrolyte may be a mix of sulfate ions as well as chloride ions when the metal anion is chloride. In such embodiments, it may be desirable to have sufficient concentration of chloride ions in the electrolyte to dissolve the metal salt but not high enough to cause undesirable ionic speciation.

In some embodiments, the electrolyte, the one or more lanthanide halides, and/or the metal compound are chosen based on the desired end product. For example, if a chlorinated hydrocarbon is desired from the reaction between the metal compound, the LAH, and the hydrocarbon, then a metal chloride is used as the metal compound, the lanthanide chloride, e.g. cerium chloride is used as the LAH, and the sodium or potassium chloride is used as the electrolyte.

In some embodiments, the metal ions used in the electrochemical systems described herein, may be chosen based on the solubility of the metal in the anode electrolyte in the presence of the one or more lanthanide halides and/or cell voltages desired for the metal oxidation from the lower oxidation state to the higher oxidation state.

It is to be understood that although the metal ion is oxidized from the lower oxidation state to the higher oxidation state in the electrochemical system and the metal ion is reduced in the halogenation system, the anode electrolyte always comprises both the metal ion in the lower oxidation state and the metal ion in the higher oxidation state. Suitable ratios of the metal ion in the lower and higher oxidation state in the anode electrolyte have been described herein.

Some examples of the metal compounds that may be used in the systems and methods of the invention include, but are not limited to, copper (I) chloride, copper (I) bromide, copper (I) iodide, iron (II) chloride, iron (II) bromide, iron (II) iodide, tin (II) chloride, tin (II) bromide, tin (II) iodide, chromium (II) chloride, chromium (II) bromide, chromium (II) iodide, zinc (II) chloride, zinc (II) bromide, etc.

Ligands

In some embodiments, an additive such as a ligand is used in conjunction with the metal ion and the one or more lanthanide halides to improve the efficiency of the metal ion oxidation inside the anode chamber and/or improve the halogenation reactions of the metal ion inside/outside the anode chamber. In some embodiments, the ligand is added along with the metal and the one or more lanthanide halides in the anode electrolyte. In some embodiments, the ligand is attached to the metal ion and/or the one or more lanthanide halides. In some embodiments, the ligand is attached to the metal ion and/or the one or more lanthanide halides by covalent, ionic and/or coordinate bonds. In some embodiments, the ligand is attached to the metal ion and/or the one or more lanthanide halides through vanderwaal attractions.

The "ligand" as used herein includes any ligand capable of enhancing the properties of the metal ion and/or the one or more lanthanide halides. In some embodiments, ligands include, but not limited to, substituted or unsubstituted aliphatic phosphine, substituted or unsubstituted aromatic phosphine, substituted or unsubstituted amino phosphine, substituted or unsubstituted crown ether, substituted or unsubstituted aliphatic nitrogen, substituted or unsubstituted cyclic nitrogen, substituted or unsubstituted aliphatic sulfur, substituted or unsubstituted cyclic sulfur, substituted or unsubstituted heterocyclic, and substituted or unsubstituted heteroaromatic. The ligands have been described in U.S. patent application Ser. No. 13/474,598, filed May 17, 2012, issued as U.S. Pat. No. 9,187,834, issued Nov. 17, 2015, which is incorporated herein by reference in its entirety.

Figure 3:
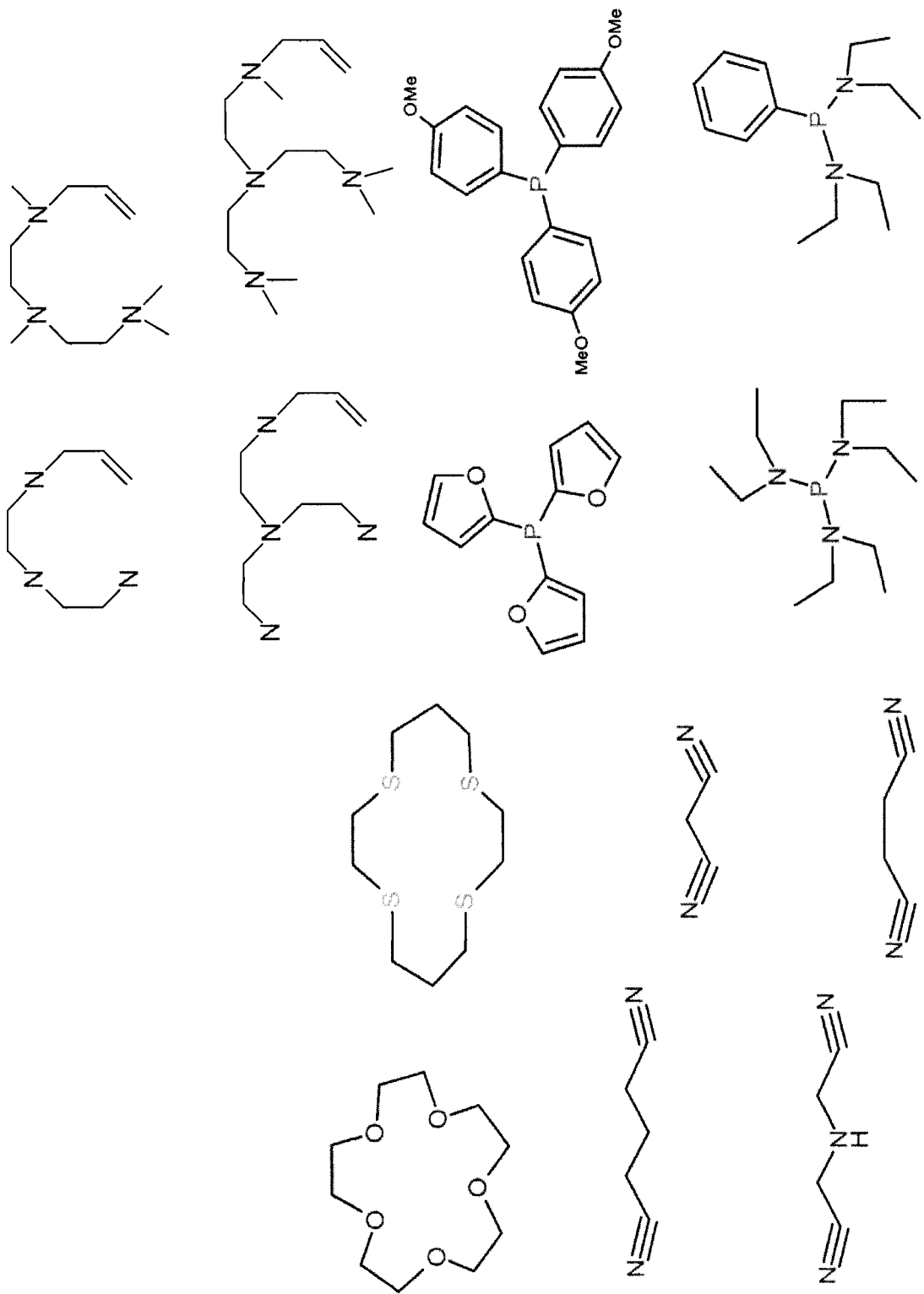
FIG. 3 is an illustration of some embodiments related to ligands.

Some examples of the ligands are illustrated in FIG. 3.

Substituted or Unsubstituted Aliphatic Nitrogen

In some embodiments, the ligand is a substituted or unsubstituted aliphatic nitrogen of formula A:

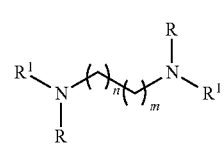

A wherein n and m independently are 0-2 and R and $R^1$ independently are H, alkyl, or substituted alkyl. In some embodiments, alkyl is methyl, ethyl, propyl, i-propyl, butyl, i-butyl, or pentyl. In some embodiments, the substituted alkyl is alkyl substituted with one or more of a group including alkenyl, halogen, amine, substituted amine, and combination thereof. In some embodiments, the substituted amine is substituted with a group selected from hydrogen and/or alkyl. Some examples of the ligands are illustrated in FIG. 3.

In some embodiments, the ligand is a substituted or unsubstituted aliphatic nitrogen of formula B:

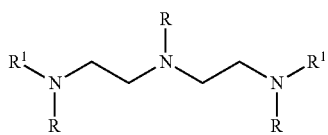

wherein R and $R^1$ independently are H, alkyl, or substituted alkyl. In some embodiments, alkyl is methyl, ethyl, propyl, i-propyl, butyl, i-butyl, or pentyl. In some embodiments, the substituted alkyl is alkyl substituted with one or more of a group including alkenyl, halogen, amine, substituted amine, and combination thereof. In some embodiments, the substituted amine is substituted with a group selected from hydrogen and/or alkyl.

In some embodiments, the ligand is a substituted or unsubstituted aliphatic nitrogen donor of formula B, wherein R and $R^1$ independently are H, $C_1$-$C_4$ alkyl, or substituted $C_1$-$C_4$ alkyl. In some embodiments, $C_1$-$C_4$ alkyl is methyl, ethyl, propyl, i-propyl, butyl, or i-butyl. In some embodiments, the substituted $C_1$-$C_4$ alkyl is $C_1$-$C_4$ alkyl substituted with one or more of a group including alkenyl, halogen, amine, substituted amine, and combination thereof. In some embodiments, the substituted amine is substituted with a group selected from hydrogen and/or $C_1$-$C_3$ alkyl.

The concentration of the ligand may be chosen based on various parameters, including but not limited to, concentration of the metal ion, concentration of LAH, solubility of the ligand etc. Some examples of ligands that are substituted or unsubstituted aliphatic nitrogen, are as illustrated in FIG. 3.

Substituted or Unsubstituted Crown Ether with O, S, P or N Heteroatoms

In some embodiments, the ligand is a substituted or unsubstituted crown ether of formula C:

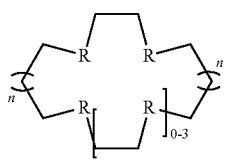

wherein R is independently O, S, P, or N; and n is 0 or 1.

In some embodiments, the ligand is a substituted or unsubstituted crown ether of formula C, wherein R is O and n is 0 or 1. In some embodiments, the ligand is a substituted or unsubstituted crown ether of formula C, wherein R is S and n is 0 or 1. In some embodiments, the ligand is a substituted or unsubstituted crown ether of formula C, wherein R is N and n is 0 or 1. In some embodiments, the ligand is a substituted or unsubstituted crown ether of formula C, wherein R is P and n is 0 or 1. In some embodiments, the ligand is a substituted or unsubstituted crown ether of formula C, wherein R is O or S, and n is 0 or 1. In some embodiments, the ligand is a substituted or unsubstituted crown ether of formula C, wherein R is O or N, and n is 0 or 1. In some embodiments, the ligand is a substituted or unsubstituted crown ether of formula C, wherein R is N or S, and n is 0 or 1. In some embodiments, the ligand is a substituted or unsubstituted crown ether of formula C, wherein R is N or P, and n is 0 or 1.

Substituted or Unsubstituted Phosphines

In some embodiments, the ligand is a substituted or unsubstituted phosphine of formula D, or an oxide thereof:

wherein $R^1$, $R^2$, and $R^3$ independently are H, alkyl, substituted alkyl, alkoxy, substituted alkoxy, aryl, substituted aryl, heteroaryl, substituted heteroaryl, amine, substituted amine, cycloalkyl, substituted cycloalkyl, heterocycloalkyl, and substituted heterocycloalkyl.

An example of an oxide of formula D is:

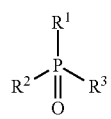

wherein $R^1$, $R^2$, and $R^3$ independently are H, alkyl, substituted alkyl, alkoxy, substituted alkoxy, aryl, substituted aryl, heteroaryl, substituted heteroaryl, amine, substituted amine, cycloalkyl, substituted cycloalkyl, heterocycloalkyl, and substituted heterocycloalkyl.

In some embodiments of the compound of formula D or an oxide thereof, $R^1$, $R^2$, and $R^3$ independently are alkyl and substituted alkyl. In some embodiments of the compound of formula D or an oxide thereof, $R^1$, $R^2$, and $R^3$ independently are alkyl and substituted alkyl wherein the substituted alkyl is substituted with group selected from alkoxy, substituted alkoxy, amine, and substituted amine. In some embodiments of the compound of formula D, or an oxide thereof, $R^1$, $R^2$, and $R^3$ independently are alkyl and substituted alkyl wherein the substituted alkyl is substituted with group selected from alkoxy and amine.

In some embodiments of the compound of formula D or an oxide thereof, $R^1$, $R^2$, and $R^3$ independently are alkoxy and substituted alkoxy. In some embodiments of the compound of formula D or an oxide thereof, $R^1$, $R^2$, and $R^3$ independently are alkoxy and substituted alkoxy wherein the substituted alkoxy is substituted with group selected from alkyl, substituted alkyl, amine, and substituted amine. In some embodiments of the compound of formula D or an oxide thereof, $R^1$, $R^2$, and $R^3$ independently are alkoxy and substituted alkoxy wherein the substituted alkoxy is substituted with group selected from alkyl and amine.

In some embodiments of the compound of formula D or an oxide thereof, $R^1$, $R^2$, and $R^3$ independently are aryl and substituted aryl. In some embodiments of the compound of formula D or an oxide thereof, $R^1$, $R^2$, and $R^3$ independently are aryl and substituted aryl wherein the substituted aryl is substituted with group selected from alkyl, substituted alkyl, alkoxy, substituted alkoxy, amine, and substituted amine. In some embodiments of the compound of formula D or an oxide thereof, $R^1$, $R^2$, and $R^3$ independently are aryl and substituted aryl wherein the substituted aryl is substituted with group selected from alkyl, alkoxy, and amine. In some embodiments of the compound of formula D or an oxide thereof, $R^1$, $R^2$, and $R^3$ independently are aryl and substituted aryl wherein the substituted aryl is substituted with group selected from alkyl and alkoxy.

In some embodiments of the compound of formula D or an oxide thereof, $R^1$, $R^2$, and $R^3$ independently are heteroaryl and substituted heteroaryl. In some embodiments of the compound of formula D or an oxide thereof, $R^1$, $R^2$, and $R^3$ independently are heteroaryl and substituted heteroaryl wherein the substituted heteroaryl is substituted with a group selected from alkyl, substituted alkyl, alkoxy, substituted alkoxy, amine, and substituted amine. In some embodiments of the compound of formula D or an oxide thereof, $R^1$, $R^2$, and $R^3$ independently are heteroaryl and substituted heteroaryl wherein the substituted heteroaryl is substituted with a group selected from alkyl, alkoxy, and amine.

In some embodiments of the compound of formula D or an oxide thereof, $R^1$, $R^2$, and $R^3$ independently are cycloalkyl and substituted cycloalkyl. In some embodiments of the compound of formula D or an oxide thereof, $R^1$, $R^2$, and $R^3$ independently are cycloalkyl and substituted cycloalkyl wherein the substituted cycloalkyl is substituted with a group selected from alkyl, substituted alkyl, alkoxy, substituted alkoxy, amine, and substituted amine. In some embodiments of the compound of formula D or an oxide thereof, $R^1$, $R^2$, and $R^3$ independently are cycloalkyl and substituted cycloalkyl wherein the substituted cycloalkyl is substituted with a group selected from alkyl, alkoxy, and amine.

In some embodiments of the compound of formula D or an oxide thereof, $R^1$, $R^2$, and $R^3$ independently are heterocycloalkyl and substituted heterocycloalkyl. In some embodiments of the compound of formula D or an oxide thereof, $R^1$, $R^2$, and $R^3$ independently are heterocycloalkyl and substituted heterocycloalkyl wherein the substituted heterocycloalkyl is substituted with a group selected from alkyl, substituted alkyl, alkoxy, substituted alkoxy, amine, and substituted amine. In some embodiments of the compound of formula D or an oxide thereof, $R^1$, $R^2$, and $R^3$ independently are heterocycloalkyl and substituted heterocycloalkyl wherein the substituted heterocycloalkyl is substituted with a group selected from alkyl, alkoxy, and amine.

In some embodiments of the compound of formula D or an oxide thereof, $R^1$, $R^2$, and $R^3$ independently are amine and substituted amine. In some embodiments of the compound of formula D or an oxide thereof, $R^1$, $R^2$, and $R^3$ independently are amine and substituted amine wherein the substituted amine is substituted with a group selected from alkyl, substituted alkyl, alkoxy, and substituted alkoxy. In some embodiments of the compound of formula D or an oxide thereof, $R^1$, $R^2$, and $R^3$ independently are amine and substituted amine wherein the substituted amine is substituted with a group selected from alkyl, and alkoxy. In some embodiments of the compound of formula D or an oxide thereof, $R^1$, $R^2$, and $R^3$ independently are amine and substituted amine wherein the substituted amine is substituted with alkyl.

In some embodiments, the ligand is a substituted or unsubstituted phosphine of formula D or an oxide thereof:

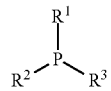

D wherein $R^1$, $R^2$, and $R^3$ independently are H, alkyl; substituted alkyl substituted with a group selected from alkoxy, substituted alkoxy, amine, and substituted amine; aryl; substituted aryl substituted with a group selected from alkyl, substituted alkyl, alkoxy, substituted alkoxy, amine, and substituted amine; heteroaryl; substituted heteroaryl substituted with a group selected from alkyl, substituted alkyl, alkoxy, substituted alkoxy, amine, and substituted amine; amine; substituted amine substituted with a group selected from alkyl, substituted alkyl, alkoxy, and substituted alkoxy; cycloalkyl; substituted cycloalkyl substituted with a group selected from alkyl, substituted alkyl, alkoxy, substituted alkoxy, amine, and substituted amine; heterocycloalkyl; and substituted heterocycloalkyl substituted with a group selected from alkyl, substituted alkyl, alkoxy, substituted alkoxy, amine, and substituted amine.

In some embodiments, the ligand is a substituted or unsubstituted phosphine of formula D or an oxide thereof:

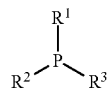

D wherein $R^1$, $R^2$, and $R^3$ independently are H, alkyl; substituted alkyl substituted with a group selected from alkoxy and amine; aryl; substituted aryl substituted with a group selected from alkyl, alkoxy, and amine; heteroaryl; substituted heteroaryl substituted with a group selected from alkyl, alkoxy, and amine; amine; substituted amine substituted with a group selected from alkyl, and alkoxy; cycloalkyl; substituted cycloalkyl substituted with a group selected from alkyl, alkoxy, and amine; heterocycloalkyl; and substituted heterocycloalkyl substituted with a group selected from alkyl, alkoxy, and amine.

Substituted or Unsubstituted Pyridines

In some embodiments, the ligand is a substituted or unsubstituted pyridine of formula E:

E wherein $R^1$ and $R^2$ independently are H, alkyl, substituted alkyl, aryl, substituted aryl, heteroaryl, substituted heteroaryl, amine, substituted amine, cycloalkyl, substituted cycloalkyl, heterocycloalkyl, and substituted heterocycloalkyl.

In some embodiments, the ligand is a substituted or unsubstituted pyridine of formula E:

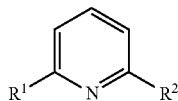

wherein R¹ and R² independently are H, alkyl, substituted alkyl, heteroaryl, substituted heteroaryl, amine, and substituted amine.

In some embodiments, the ligand is a substituted or unsubstituted pyridine of formula E, wherein R¹ and R² independently are H, alkyl, and substituted alkyl wherein substituted alkyl is substituted with a group selected from alkoxy, substituted alkoxy, amine, and substituted amine. In some embodiments, the ligand is a substituted or unsubstituted pyridine of formula E, wherein R¹ and R² independently are H, alkyl, and substituted alkyl wherein substituted alkyl is substituted with a group selected from amine, and substituted amine wherein substituted amine is substituted with an alkyl, heteroaryl or a substituted heteroaryl.

In some embodiments, the ligand is a substituted or unsubstituted pyridine of formula E, wherein R¹ and R² independently are heteroaryl and substituted heteroaryl. In some embodiments, the ligand is a substituted or unsubstituted pyridine of formula E, wherein R¹ and R² independently are heteroaryl and substituted heteroaryl substituted with alkyl, alkoxy or amine.

In some embodiments, the ligand is a substituted or unsubstituted pyridine of formula E, wherein R¹ and R² independently are amine and substituted amine. In some embodiments, the ligand is a substituted or unsubstituted pyridine of formula E, wherein R¹ and R² independently are amine and substituted amine wherein substituted amine is substituted with an alkyl, heteroaryl or a substituted heteroaryl.

In some embodiments, the ligand is a substituted or unsubstituted pyridine of formula E:

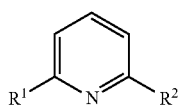

wherein R¹ and R² independently are H; alkyl; substituted alkyl substituted with a group selected from amine and substituted amine; heteroaryl; substituted heteroaryl substituted with alkyl, alkoxy or amine; amine; and substituted amine substituted with an alkyl, heteroaryl or a substituted heteroaryl.

Substituted or Unsubstituted Dinitriles

In some embodiments, the ligand is a substituted or unsubstituted dinitrile of formula F:

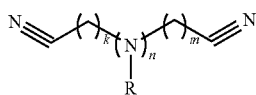

wherein R is hydrogen, alkyl, or substituted alkyl; n is 0-2; m is 0-3; and k is 1-3.

In some embodiments, the ligand is a substituted or unsubstituted dinitrile of formula F, wherein R is hydrogen, alkyl, or substituted alkyl substituted with alkoxy or amine; n is 0-1; m is 0-3; and k is 1-3.

In some embodiments, the ligand is a substituted or unsubstituted dinitrile of formula F, wherein R is hydrogen or alkyl; n is 0-1; m is 0-3; and k is 1-3.

In one aspect, there is provided a composition comprising an aqueous medium comprising a ligand selected from substituted or unsubstituted phosphine, substituted or unsubstituted crown ether, substituted or unsubstituted aliphatic nitrogen, substituted or unsubstituted pyridine, substituted or unsubstituted dinitrile, and combination thereof; the LAH as described herein; and the metal halide.

In one aspect, there is provided a composition comprising an aqueous medium comprising a ligand selected from substituted or unsubstituted phosphine, substituted or unsubstituted crown ether, substituted or unsubstituted aliphatic nitrogen, substituted or unsubstituted pyridine, substituted or unsubstituted dinitrile, and combination thereof; the LAH as described herein; and a metal ion in the metal halide selected from iron, chromium, copper, tin, silver, cobalt, uranium, lead, mercury, vanadium, bismuth, titanium, ruthenium, osmium, europium, zinc, cadmium, gold, nickel, palladium, platinum, rhodium, iridium, manganese, technetium, rhenium, molybdenum, tungsten, niobium, tantalum, zirconium, hafnium, and combination thereof.

In some embodiments, the foregoing compositions further comprise salt (salts have been described herein).

In one aspect, there is provided a composition comprising an aqueous medium comprising a ligand selected from substituted or unsubstituted phosphine, substituted or unsubstituted crown ether, substituted or unsubstituted aliphatic nitrogen, substituted or unsubstituted pyridine, substituted or unsubstituted dinitrile, and combination thereof; the metal halide; the LAH; the salt; and an unsaturated or saturated hydrocarbon.

In some embodiments of the methods and systems provided herein, the ligand is:
sulfonated bathocuprine;
pyridine;
tris(2-pyridylmethyl)amine;
glutaronitrile;
iminodiacetonitrile;
malononitrile;
succinonitrile;
tris(diethylamino)phosphine;
tris(dimethylamino)phosphine;
tri(2-furyl)phosphine;
tris(4-methoxyphenyl)phosphine;
bis(diethylamino)phenylphosphine;
tris(N,N-tetramethylene)phosphoric acid triamide;
di-tert-butyl N,N-diisopropyl phosphoramidite;
diethylphosphoramidate;
hexamethylphosphoramide;
diethylenetriamine;
tris(2-aminoethyl)amine;
N,N,N',N',N''-pentamethyldiethylenetriamine;
15-Crown-5;
1,4,8,11-tetrathiacyclotetradecane; and
salt, or stereoisomer thereof.

As used herein, "alkenyl" refers to linear or branched hydrocarbyl having from 2 to 10 carbon atoms and in some embodiments from 2 to 6 carbon atoms or 2 to 4 carbon atoms and having at least 1 site of vinyl unsaturation (>C=C<). For example, ethenyl, propenyl, 1,3-butadienyl, and the like.

As used herein, "alkoxy" refers to —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

As used herein, "alkyl" refers to monovalent saturated aliphatic hydrocarbyl groups having from 1 to 10 carbon atoms and, in some embodiments, from 1 to 6 carbon atoms. "$C_x$-$C_y$ alkyl" refers to alkyl groups having from x to y carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

As used herein, "amino" or "amine" refers to the group —$NH_2$.

As used herein, "aryl" refers to an aromatic group of from 6 to 14 carbon atoms and no ring heteroatoms and having a single ring (e.g., phenyl) or multiple condensed (fused) rings (e.g., naphthyl or anthryl).

As used herein, "cycloalkyl" refers to a saturated or partially saturated cyclic group of from 3 to 14 carbon atoms and no ring heteroatoms and having a single ring or multiple rings including fused, bridged, and spiro ring systems. Examples of cycloalkyl groups include, for instance, cyclopropyl, cyclobutyl, cyclopentyl, cyclooctyl, and cyclohexenyl.

As used herein, "halo" or "halogen" refers to fluoro, chloro, bromo, and iodo.

As used herein, "heteroaryl" refers to an aromatic group of from 1 to 6 heteroatoms selected from the group consisting of oxygen, nitrogen, and sulfur and includes single ring (e.g. furanyl) and multiple ring systems (e.g. benzimidazol-2-yl and benzimidazol-6-yl). The heteroaryl includes, but is not limited to, pyridyl, furanyl, thienyl, thiazolyl, isothiazolyl, triazolyl, imidazolyl, isoxazolyl, pyrrolyl, pyrazolyl, pyridazinyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, quinazolinonyl, benzimidazolyl, benzisoxazolyl, or benzothienyl.

As used herein, "heterocycloalkyl" refers to a saturated or partially saturated cyclic group having from 1 to 5 heteroatoms selected from the group consisting of nitrogen, sulfur, or oxygen and includes single ring and multiple ring systems including fused, bridged, and spiro ring systems. The heterocyclyl includes, but is not limited to, tetrahydropyranyl, piperidinyl, N-methylpiperidin-3-yl, piperazinyl, N-methylpyrrolidin-3-yl, 3-pyrrolidinyl, 2-pyrrolidon-1-yl, morpholinyl, and pyrrolidinyl.

As used herein, "substituted alkoxy" refers to —O-substituted alkyl wherein substituted alkyl is as defined herein.

As used herein, "substituted alkyl" refers to an alkyl group having from 1 to 5 and, in some embodiments, 1 to 3 or 1 to 2 substituents selected from the group consisting of alkenyl, halogen, —OH, —COOH, amino, substituted amino, wherein said substituents are as defined herein.

As used herein, "substituted amino" or "substituted amine" refers to the group —$NR^{11}R^{11}$ where $R^{10}$ and $R^{11}$ are independently selected from the group consisting of hydrogen, alkyl, substituted alkyl, aryl, substituted aryl, heteroaryl, and substituted heteroaryl.

As used herein, "substituted aryl" refers to aryl groups which are substituted with 1 to 8 and, in some embodiments, 1 to 5, 1 to 3, or 1 to 2 substituents selected from the group consisting of alkyl, substituted alkyl, alkoxy, substituted alkoxy, amine, substituted amine, alkenyl, halogen, —OH, and —COOH, wherein said substituents are as defined herein.

As used herein, "substituted cycloalkyl" refers to a cycloalkyl group, as defined herein, having from 1 to 8, or 1 to 5, or in some embodiments 1 to 3 substituents selected from the group consisting of alkyl, substituted alkyl, alkoxy, substituted alkoxy, amine, substituted amine, alkenyl, halogen, —OH, and —COOH, wherein said substituents are as defined herein.

As used herein, "substituted heteroaryl" refers to heteroaryl groups that are substituted with from 1 to 5, or 1 to 3, or 1 to 2 substituents selected from the group consisting of the substituents defined for substituted aryl.

As used herein, "substituted heterocycloalkyl" refers to heterocyclic groups, as defined herein, that are substituted with from 1 to 5 or in some embodiments 1 to 3 of the substituents as defined for substituted cycloalkyl.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substitutions is three. Similarly, it is understood that the above definitions are not intended to include impermissible substitution patterns (e.g., methyl substituted with 5 chloro groups). Such impermissible substitution patterns are well known to the skilled artisan.

In some embodiments, the concentration of the ligand in the electrochemical cell is dependent on the concentration of the metal ion in the lower and/or the higher oxidation state and/or the concentration of LAH. In some embodiments, the concentration of the ligand is between 0.25M-5M; or between 0.25M-4M; or between 0.25M-3M; or between 0.5M-5M; or between 0.5M-4M; or between 0.5M-3M; or between 0.5M-2.5M; or between 0.5M-2M; or between 0.5M-1.5M; or between 0.5M-1M; or between 1M-2M; or between 1.5M-2.5M; or between 1.5M-2M.

Anode Electrolyte or Anolyte and Cathode Electrolyte or Catholyte

In some embodiments, the electrolyte including the catholyte or the cathode electrolyte and/or the anolyte or the anode electrolyte, or the third electrolyte disposed between AEM and CEM, in the systems and methods provided herein includes water, also described herein as the aqueous medium. The water comprises metal halide and the one or more lanthanide halides and optionally salt. The electrochemical systems and methods described herein are carried out in more than 5 wt % water or more than 6 wt % water or the aqueous medium. In some embodiments, the electrochemical systems and methods described herein include the aqueous medium containing more than 5 wt % water. In some embodiments, the aqueous medium includes more than 5 wt % water; or more than 6 wt %; or more than 8 wt % water; or more than 10 wt % water; or more than 25 wt % water; or more than 50 wt % water; or between 5-70 wt % water; or between 5-60 wt % water; or between 5-50 wt % water; or between 6-70 wt % water; or between 6-60 wt % water; or between 6-50 wt % water; or between 10-50 wt % water; or between 20-50 wt % water. In some embodiments, the aqueous medium may comprise a water soluble organic solvent.

In some embodiments, the electrolyte including the cathode electrolyte and/or the anode electrolyte and/or the third electrolyte, is a salt containing water including water containing more than 1% chloride content, such as, NaCl; or more than 10% NaCl; or more than 20% NaCl; or more than 30% NaCl; or more than 40% NaCl; or more than 50% NaCl; or more than 60% NaCl; or more than 70% NaCl; or between 1-70% NaCl; or between 1-60% NaCl; or between 1-50% NaCl; or between 1-40% NaCl; or between 1-30% NaCl; or between 1-20% NaCl; or between 1-10% NaCl; or between 10-70% NaCl; or between 10-60% NaCl; or between 10-50% NaCl; or between 30-70% NaCl; or between 30-60% NaCl; or between 30-50% NaCl; or between 40-50% NaCl. Various other salts have been described herein and the above concentrations apply to any of the alkali metal or alkaline earth metal halides or chlorides. The percentages recited herein include wt % or wt/wt %. It is to be understood that all the electrochemical systems described herein that contain sodium chloride can be replaced with other suitable electrolytes, such as, but not limited to, ammonium chloride, calcium chloride, sodium bromide, sodium iodide, or the like.

In some embodiments of the methods and systems described herein, the amount of total metal halide in the anode electrolyte or the amount of copper halide in the anode electrolyte or the amount of iron halide in the anode electrolyte or the amount of chromium halide in the anode electrolyte or the amount of tin halide in the anode electrolyte or the amount of platinum halide or the amount of metal halide that is contacted with the unsaturated or saturated hydrocarbon is between 1-12M; or between 1-10M; or between 1-8M; or between 1-5M; or between 4-12M; or between 4-10M; or between 4-6M; or between 5-10M; or between 6-12M; or between 6-10M. In some embodiments, the amount of total concentration in the anode electrolyte, as described above, is the amount of the metal halide in the lower oxidation state plus the amount of the metal halide in the higher oxidation state; or the total amount of the metal halide in the higher oxidation state; or the total amount of the metal halide in the lower oxidation state.

The amount of lanthanide halide has been described herein above.

The anode electrolyte may optionally contain 0.01-0.1M hydrochloric acid. In some embodiments of the methods and systems described herein, the anode electrolyte may contain salt in addition to the metal ion. The salt has been described herein. The salt cation includes, but is not limited to, alkaline metal ions and/or alkaline earth metal ions, such as but not limited to, lithium, sodium, calcium, magnesium, etc. The amount of the salt added to the anode electrolyte may be between 0.01-5M; or between 0.01-1M; or between 0.05-1M; or between 0.5-2M; or between 1-5M.

In some embodiments, the anode electrolyte and the cathode electrolyte in the electrochemical cell, in the methods and systems provided herein, are operated at room temperature or at elevated temperatures, such as, e.g., at more than 70° C., or more than 80° C., or between 30-100° C. As described herein, it is contemplated that the LAH facilitates solubility of the metal halides at lower temperatures in the electrochemical cell thereby saving energy cost and maintaining the integrity of the IEMs.

Cathode

As illustrated in FIGS. 1 and 2, the electrochemical system 100 includes a cathode in contact with the cathode electrolyte or catholyte where the hydroxide is formed in the cathode electrolyte. The system 100 also includes an anode in contact with the anode electrolyte that converts metal ions in the lower oxidation state ($M^{L+}$) to metal ions in the higher oxidation states ($M^{H+}$) in the presence of the one or more lanthanide halides. Following are the reactions that take place at the cathode and the anode:

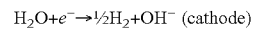
$H_2O + e^- \rightarrow \frac{1}{2} H_2 + OH^-$ (cathode)

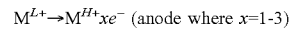
$M^{L+} \rightarrow M^{H+} xe^-$ (anode where x=1-3)

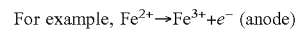
For example, $Fe^{2+} \rightarrow Fe^{3+} + e^-$ (anode)

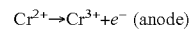
$Cr^{2+} \rightarrow Cr^{3+} + e^-$ (anode)

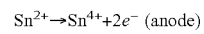
$Sn^{2+} \rightarrow Sn^{4+} + 2e^-$ (anode)

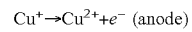
$Cu^+ \rightarrow Cu^{2+} + e^-$ (anode)

This electrochemical system includes a cathode that forms hydroxide ions and hydrogen gas at the cathode. The hydrogen gas may be vented out or captured and stored for commercial purposes. The hydroxide ion formed at the cathode combines with alkali metal cations and/or alkaline earth metal cations which migrate from anolyte or from the third electrolyte. For example only, the hydroxide ions formed at the cathode combine with sodium ions to form sodium hydroxide.

In some embodiments, the cathode used in the electrochemical systems of the invention, is a hydrogen gas producing cathode that does not form an alkali. For example, the electrochemical system 100 includes a cathode in contact with the cathode electrolyte where the hydrochloric acid delivered to the cathode electrolyte is transformed to hydrogen gas in the cathode electrolyte. Following are the reactions that may take place at the cathode and the anode:

$2H^+ + 2e^- \rightarrow H_2$ (cathode)

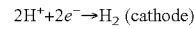
$M^{L+} \rightarrow M^{H+} xe^-$ (anode where x=1-3)

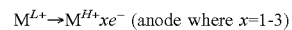
For example, $Fe^{2+} \rightarrow Fe^{3+} + e^-$ (anode)

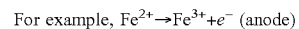
$Cr^{2+} \rightarrow Cr^{3+} + e^-$ (anode)

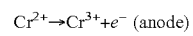
$Sn^{2+} \rightarrow Sn^{4+} + 2e^-$ (anode)

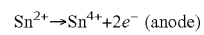
$Cu^+ \rightarrow Cu^{2+} + e^-$ (anode)

In some embodiments, the cathode in the electrochemical systems of the invention may be a gas-diffusion cathode. In some embodiments, the cathode in the electrochemical systems of the invention may be a gas-diffusion cathode forming an alkali at the cathode. In some embodiments, the gas-diffusion cathode is an oxygen depolarized cathode (ODC). In some embodiments, the gas-diffusion cathode does not form a gas. As used herein, the "gas-diffusion cathode," or "gas-diffusion electrode," or other equivalents thereof include any electrode capable of reacting a gas to form ionic species. Such gas-diffusion cathode may be called gas-diffusion electrode, oxygen consuming cathode, oxygen reducing cathode, oxygen breathing cathode, oxygen depolarized cathode, and the like. In some embodiments, the electrochemical system 100 includes a gas diffusion cathode in contact with the cathode electrolyte and the anode in contact with the anode electrolyte. Following are the reactions that may take place at the anode and the cathode.

$H_2O + \frac{1}{2} O_2 + 2e^- \rightarrow 2OH^-$ (cathode)

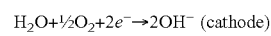
$M^{L+} \rightarrow M^{H+} xe^-$ (anode where x=1-3)

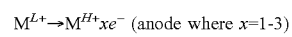
For example, $Fe^{2+} \rightarrow Fe^{3+} + e^-$ (anode)

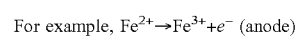
$Cr^{2+} \rightarrow Cr^{3+} + e^-$ (anode)

$Sn^{2+} \rightarrow Sn^{4+} + 2e^-$ (anode)

$Cu^+ \rightarrow Cu^{2+} + e^-$ (anode)

The hydroxide ion formed at the cathode combines with alkali metal or alkaline earth metal cations, e.g. sodium ions to form sodium hydroxide. The oxygen at the cathode may be atmospheric air or any commercial available source of oxygen.

In some embodiments, the combination of the gas diffusion cathode (e.g., ODC) and the anode in the electrochemical cell may result in the generation of water in the cathode chamber. In some embodiments, the electrochemical system 100 includes a gas diffusion cathode in contact with the cathode electrolyte and the anode in contact with the anode electrolyte. Following are the reactions that may take place at the anode and the cathode.

$2H^+ + \frac{1}{2}O_2 + 2e^- \rightarrow H_2$ (cathode)

$M^{L+} \rightarrow M^{H+}xe^-$ (anode where $x$=1-3)

For example, $Fe^{2+} \rightarrow Fe^{3+} + e^-$ (anode)

$Cr^{2+} \rightarrow Cr^{3+} + e^-$ (anode)

$Sn^{2+} \rightarrow Sn^{4+} + 2e^-$ (anode)

$Cu^+ \rightarrow Cu^{2+} + e^-$ (anode)

The oxygen at the cathode may be atmospheric air or any commercial available source of oxygen.

In some embodiments, the systems provided herein further include an oxygen gas supply or delivery system operably connected to the cathode chamber. The oxygen gas delivery system is configured to provide oxygen gas to the gas-diffusion cathode. In some embodiments, the oxygen gas delivery system is configured to deliver gas to the gas-diffusion cathode where reduction of the gas is catalyzed to hydroxide ions. In some embodiments, the oxygen gas and water are reduced to hydroxide ions; un-reacted oxygen gas in the system is recovered; and re-circulated to the cathode. The oxygen gas may be supplied to the cathode using any means for directing the oxygen gas from the external source to the cathode. Such means for directing the oxygen gas from the external source to the cathode or the oxygen gas delivery system are well known in the art and include, but not limited to, pipe, duct, conduit, and the like. In some embodiments, the system or the oxygen gas delivery system includes a duct that directs the oxygen gas from the external source to the cathode.

It is to be understood that the oxygen gas may be directed to the cathode from the bottom of the cell, top of the cell or sideways. In some embodiments, the oxygen gas is directed to the back side of the cathode where the oxygen gas is not in direct contact with the catholyte. In some embodiments, the oxygen gas may be directed to the cathode through multiple entry ports. The source of oxygen that provides oxygen gas to the gas-diffusion cathode, in the methods and systems provided herein, includes any source of oxygen known in the art. Such sources include, without limitation, ambient air, commercial grade oxygen gas from cylinders, oxygen gas obtained by fractional distillation of liquefied air, oxygen gas obtained by passing air through a bed of zeolites, oxygen gas obtained from electrolysis of water, oxygen obtained by forcing air through ceramic membranes based on zirconium dioxides by either high pressure or electric current, chemical oxygen generators, oxygen gas as a liquid in insulated tankers, or combination thereof. In some embodiments, the source of oxygen may also provide carbon dioxide gas. In some embodiments, the oxygen from the source of oxygen gas may be purified before being administered to the cathode chamber. In some embodiments, the oxygen from the source of oxygen gas is used as is in the cathode chamber.

In one aspect, there are provided methods and systems as described herein that include contacting carbon dioxide with the cathode electrolyte either inside the cathode chamber or outside the cathode chamber. In some embodiments, the carbon from the source of carbon is treated with the cathode electrolyte to form a solution of dissolved carbon dioxide in the alkali of the cathode electrolyte. The alkali present in the cathode electrolyte may facilitate dissolution of carbon dioxide in the solution. The solution with dissolved carbon dioxide includes carbonic acid, bicarbonate, carbonate, or any combination thereof. In such method and system, the carbon from the source of carbon includes gaseous carbon dioxide from an industrial process or a solution of carbon dioxide from a gas/liquid contactor which is in contact with the gaseous carbon dioxide from the industrial process. In some embodiments of the systems including the contactor, the cathode chamber includes bicarbonate and carbonate ions in addition to hydroxide ions.

Anode

In some embodiments, the anode may contain a corrosion stable, electrically conductive base support. Such as, but not limited to, amorphous carbon, such as carbon black, fluorinated carbons like the specifically fluorinated carbons described in U.S. Pat. No. 4,908,198 and available under the trademark SFC™ carbons. Other examples of electrically conductive base materials include, but not limited to, sub-stoichiometric titanium oxides, such as, Magneli phase sub-stoichiometric titanium oxides having the formula $TiO_x$ wherein x ranges from about 1.67 to about 1.9. For example, titanium oxide $Ti_4O_7$. In some embodiments, carbon based materials provide a mechanical support for the GDE or as blending materials to enhance electrical conductivity but may not be used as catalyst support to prevent corrosion.

In some embodiments, the gas-diffusion electrodes or general electrodes described herein contain an electrocatalyst for aiding in electrochemical dissociation, e.g. reduction of oxygen at the cathode. Examples of electrocatalysts include, but not limited to, highly dispersed metals or alloys of the platinum group metals, such as platinum, palladium, ruthenium, rhodium and iridium (e.g. titanium mesh coated with PtIr mixed metal oxide or titanium coated with galvanized platinum); electrocatalytic metal oxides; organometallic macrocyclic compounds, and other electrocatalysts well known in the art for electrochemical reduction of oxygen.

In some embodiments, the electrodes described herein, relate to porous homogeneous composite structures as well as heterogeneous, layered type composite structures wherein each layer may have a distinct physical and compositional make-up, e.g. porosity and electroconductive base to prevent flooding, and loss of the three phase interface, and resulting electrode performance.

The electrodes provided herein may include anodes and cathodes having porous polymeric layers on or adjacent to the anolyte or catholyte solution side of the electrode which may assist in decreasing penetration and electrode fouling. Stable polymeric resins or films may be included in a composite electrode layer adjacent to the anolyte comprising resins formed from non-ionic polymers, such as polystyrene, polyvinyl chloride, polysulfone, etc., or ionic-type charged polymers like those formed from polystyrenesulfonic acid, sulfonated copolymers of styrene and vinylbenzene, carboxylated polymer derivatives, sulfonated or carboxylated polymers having partially or totally fluorinated hydrocarbon chains and aminated polymers like polyvinylpyridine. Stable microporous polymer films may also be included on the dry side to inhibit electrolyte penetration. In some embodiments, the gas-diffusion cathodes includes such cathodes known in the art that are coated with high surface area coatings of precious metals such as gold and/or silver, precious metal alloys, nickel, and the like.

In some embodiments, the anode in the electrochemical cell is a porous corrugated anode in combination with a flat porous electrode. Such corrugated electrode has been described in U.S. patent application Ser. No. 15/605,844, filed May 25, 2017, which is incorporated herein by reference in its entirety.

Ion Exchange Membrane

In some embodiments, the cathode electrolyte and the anode electrolyte are separated in part or in full by an ion exchange membrane. In some embodiments, the ion exchange membrane is an anion exchange membrane (AEM) or a cation exchange membrane (CEM). In some embodiments, the cation exchange membranes in the electrochemical cell, as disclosed herein, are conventional and are available from, for example, Asahi Kasei of Tokyo, Japan; or from Membrane International of Glen Rock, N.J., or DuPont, in the USA. Examples of CEM include, but are not limited to, N2030WX (Dupont), F8020/F8080 (Flemion), and F6801 (Aciplex). CEMs that are desirable in the methods and systems of the invention have minimal resistance loss, greater than 90% selectivity, and high stability in concentrated caustic. AEMs, in the methods and systems provided herein, are exposed to concentrated metallic salt anolytes, the LAH, and saturated brine stream. It is desirable for the AEM to allow passage of salt ion such as chloride ion to the anolyte but reject the metallic ion species and lanthanide ions from the anolyte. In some embodiments, metallic salts may form various ion species (cationic, anionic, and/or neutral) including but not limited to, $MCl^+$, $MCl_2^-$, $MCl_2^0$, $M^{2+}$ etc. and it is desirable for such complexes to not pass through AEM or not foul the membranes.

Examples of cationic exchange membranes include, but not limited to, cationic membrane consisting of a perfluorinated polymer containing anionic groups, for example sulphonic and/or carboxylic groups. However, it may be appreciated that in some embodiments, depending on the need to restrict or allow migration of a specific cation or an anion species between the electrolytes, a cation exchange membrane that is more restrictive and thus allows migration of one species of cations while restricting the migration of another species of cations may be used as, e.g., a cation exchange membrane that allows migration of sodium ions into the cathode electrolyte from the anode electrolyte while restricting migration of other ions from the anode electrolyte into the cathode electrolyte, may be used. Similarly, in some embodiments, depending on the need to restrict or allow migration of a specific anion species between the electrolytes, an anion exchange membrane that is more restrictive and thus allows migration of one species of anions while restricting the migration of another species of anions may be used as, e.g., an anion exchange membrane that allows migration of chloride ions into the anode electrolyte from the cathode electrolyte while restricting migration of hydroxide ions from the cathode electrolyte into the anode electrolyte, may be used. Such restrictive cation and/or anion exchange membranes are commercially available and can be selected by one ordinarily skilled in the art.

In some embodiments, the membranes should be selected such that they can function in an acidic and/or basic electrolytic solution as appropriate. Other desirable characteristics of the membranes include high ion selectivity, low ionic resistance, high burst strength, and high stability in an acidic electrolytic solution in a temperature range of 0° C. to 100° C. or higher, or a alkaline solution in similar temperature range may be used. In some embodiments, it is desirable that the ion exchange membrane prevents the transport of the metal and lanthanide ion from the anolyte to the catholyte. In some embodiments, the membrane may be stable and functional for a desirable length of time in the system, e.g., several days, weeks or months or years at temperatures in the range of 0° C. to 90° C. and higher and/or lower.

The ohmic resistance of the membranes may affect the voltage drop across the anode and cathode, e.g., as the ohmic resistance of the membranes increase, the voltage across the anode and cathode may increase, and vice versa. Membranes that can be used include, but are not limited to, membranes with relatively low ohmic resistance and relatively high ionic mobility; and membranes with relatively high hydration characteristics that increase with temperatures, and thus decreasing the ohmic resistance. By selecting membranes with lower ohmic resistance known in the art, the voltage drop across the anode and the cathode at a specified temperature can be lowered.

Scattered through membranes may be ionic channels including acid groups. These ionic channels may extend from the internal surface of the matrix to the external surface and the acid groups may readily bind water in a reversible reaction as water-of-hydration. This binding of water as water-of-hydration may follow first order reaction kinetics, such that the rate of reaction is proportional to temperature. Consequently, membranes can be selected to provide a relatively low ohmic and ionic resistance while providing for improved strength and resistance in the system for a range of operating temperatures.

In some embodiments, the AEM used in the methods and systems of the invention, is resistant to the organic compounds (such as ligands or hydrocarbons) such that AEM does not interact with the organics and/or the AEM does not react or absorb metal ions. This can be achieved, for example only, by using a polymer that does not contain a free radical or anion available for reaction with organics or with metal ions. For example only, a fully quarternized amine containing polymer may be used as an AEM.

Voltage

As used herein, the "voltage" includes a voltage or a bias applied to or drawn from an electrochemical cell that drives a desired reaction between the anode and the cathode in the electrochemical cell. In some embodiments, the desired reaction may be the electron transfer between the anode and the cathode such that an alkaline solution, water, or hydrogen gas is formed in the cathode electrolyte and the metal ion is oxidized at the anode. In some embodiments, the desired reaction may be the electron transfer between the anode and the cathode such that the metal ion in the higher oxidation state is formed in the anode electrolyte from the metal ion in the lower oxidation state. The voltage may be applied to the electrochemical cell by any means for applying the current across the anode and the cathode of the electrochemical cell. Such means are well known in the art and include, without limitation, devices, such as, electrical power source, fuel cell, device powered by sun light, device powered by wind, and combination thereof. The type of electrical power source to provide the current can be any power source known to one skilled in the art. For example, in some embodiments, the voltage may be applied by connecting the anodes and the cathodes of the cell to an external direct current (DC) power source. The power source can be an alternating current (AC) rectified into DC. The DC power source may have an adjustable voltage and current to apply a requisite amount of the voltage to the electrochemical cell.

In some embodiments, the current applied to the electrochemical cell is at least 50 mA/cm$^2$; or at least 100 mA/cm$^2$; or at least 150 mA/cm$^2$; or at least 200 mA/cm$^2$; or at least 500 mA/cm$^2$; or at least 1000 mA/cm$^2$; or between 100-1000 mA/cm$^2$; or between 100-500 mA/cm$^2$; or between 200-500 mA/cm$^2$; or between 500-1000 mA/cm$^2$.

In some embodiments, the cell runs at voltage of between 0-3V when the applied current is 100-250 mA/cm$^2$ or 100-150 mA/cm$^2$ or 100-200 mA/cm$^2$ or 100-300 mA/cm$^2$ or 100-400 mA/cm$^2$ or 100-500 mA/cm$^2$ or 150-200 mA/cm$^2$ or 200-150 mA/cm$^2$ or 200-300 mA/cm$^2$ or 200-400 mA/cm$^2$ or 200-500 mA/cm$^2$ or 150 mA/cm$^2$ or 200 mA/cm$^2$ or 300 mA/cm$^2$ or 400 mA/cm$^2$ or 500 mA/cm$^2$ or 600 mA/cm$^2$.

In some embodiments, the systems and methods provided herein further include a percolator and/or a spacer between the anode and the ion exchange membrane and/or the cathode and the ion exchange membrane. In some embodiments, the system further includes a separator operably connected to the reactor that separates the product such as acid or the halogenated hydrocarbon from the metal ion in the lower oxidation state.

In one aspect, the unsaturated or saturated hydrocarbon may be administered to the anode chamber itself where the metal halide with metal in the higher oxidation state and the one or more lanthanide halides react with the unsaturated or saturated hydrocarbon to form respective products inside the anode chamber. In some embodiments, the unsaturated or saturated hydrocarbon may be administered to the anode chamber where the metal chloride with metal in the higher oxidation state and the one or more lanthanide halides react with the unsaturated or saturated hydrocarbon to form chlorohydrocarbon. Such systems include the unsaturated or saturated hydrocarbon delivery system which is operably connected to the anode chamber and is configured to deliver the unsaturated or saturated hydrocarbon to the anode chamber. The unsaturated or saturated hydrocarbon may be a solid, liquid, or a gas. The unsaturated or saturated hydrocarbon may be supplied to the anode using any means for directing the unsaturated or saturated hydrocarbon from the external source to the anode chamber. Such means for directing the unsaturated or saturated hydrocarbon from the external source to the anode chamber or the unsaturated or saturated hydrocarbon delivery system are well known in the art and include, but not limited to, pipe, tanks, duct, conduit, and the like. It is to be understood that the unsaturated or saturated hydrocarbon may be directed to the anode from the bottom of the cell, top of the cell or sideways. The system may also include a gas diffusion layer (GDL). The anode electrolyte may be in contact with the anode on one side and the GDL on the other side. In some embodiments, the anode may convert metal ions from the lower oxidation state to the metal ions in the higher oxidation states in the presence of the one or more lanthanide halides. For example, the anode may convert metal ions from 1+ oxidation state to 2+ oxidation state. The Cu$^{2+}$ ions may combine with chloride ions to form CuCl$_2$. The ethylene gas may be pressurized into a gaseous chamber on one side of the GDL. The ethylene gas may then diffuse through the gas diffusion layer and react with metal chloride in the higher oxidation state and the one or more lanthanide halides to form chlorohydrocarbon, such as ethylene dichloride. The metal chloride CuCl$_2$ in turn may undergo reduction to lower oxidation state to form CuCl. In some embodiments, the anode electrolyte may be withdrawn and the ethylene dichloride may be separated from the anode electrolyte using separation techniques well known in the art, including, but not limited to, filtration, vacuum distillation, fractional distillation, fractional crystallization, ion exchange resin, etc. In some embodiments, the anode chamber may be vented to remove the gaseous ethylene or gaseous byproducts.

Halogenation Methods and Systems

In some embodiments, the metal halide with the metal ion in the higher oxidation state in the anode electrolyte of the electrochemical systems of FIGS. 1 and 2 may be reacted with unsaturated or saturated hydrocarbons in the presence of the one or more lanthanide halides to form one or more products comprising halohydrocarbons. For example, the metal chloride, metal bromide, metal iodide, etc. may result in corresponding chlorohydrocarbons, bromohydrocarbons, iodohydrocarbons, after the reaction of the unsaturated or saturated hydrocarbons with the metal halide. In some embodiments, the reaction of metal halide with the unsaturated or saturated hydrocarbons results in the generation of the above described products as well as the reduction of the metal halide to the lower oxidation state. The metal halide with the metal ion in the lower oxidation state may then be re-circulated back to the electrochemical system for the generation of the metal ions in the higher oxidation state.

The "halohydrocarbon" or "halogenated hydrocarbon" as used herein, includes halo substituted hydrocarbons where halo may be any number of halogens that can be attached to the hydrocarbon based on permissible valency. The halogens include fluoro, chloro, bromo, and iodo. The examples of halohydrocarbons include chlorohydrocarbons, bromohydrocarbons, and iodohydrocarbons. The chlorohydrocarbons include, but not limited to, monochlorohydrocarbons, dichlorohydrocarbons, trichlorohydrocarbons, etc.

The "unsaturated hydrocarbon" as used herein, includes a hydrocarbon with unsaturated carbon or hydrocarbon with at least one double and/or at least one triple bond between adjacent carbon atoms. The unsaturated hydrocarbon may be linear, branched, or cyclic (aromatic or non-aromatic). For example, the hydrocarbon may be olefinic, acetylenic, non-aromatic such as cyclohexene, aromatic group or a substituted unsaturated hydrocarbon such as, but not limited to, halogenated unsaturated hydrocarbon. The hydrocarbons with at least one double bond called olefins or alkenes, have a general formula of an unsubstituted alkene as $C_nH_{2n}$ where n is 2-20 or 2-10 or 2-8, or 2-5. In some embodiments, one or more hydrogens on the alkene may be further substituted with other functional groups such as but not limited to, halogen (including chloro, bromo, iodo, and fluoro), carboxylic acid (—COOH), hydroxyl (—OH), amines, etc. The unsaturated hydrocarbons include all the isomeric forms of unsaturation, such as, but not limited to, cis and trans isomers, E and Z isomers, positional isomers etc.

Examples of substituted or unsubstituted alkenes include, but not limited to, ethylene, chloro ethylene, bromo ethylene, iodo ethylene, propylene, chloro propylene, hydroxyl propylene, 1-butylene, 2-butylene (cis or trans), isobutylene, 1,3-butadiene, pentylene, hexene, cyclopropylene, cyclobutylene, cyclohexene, etc. The hydrocarbons with at least one triple bond called alkynes have a general formula of an unsubstituted alkyne as $C_nH_{2n-2}$ where n is 2-10 or 2-8, or 2-5. In some embodiments, one or more hydrogens on the alkyne may be further substituted with other functional groups such as but not limited to, halogen, carboxylic acid, hydroxyl, etc.

In some embodiments, the unsaturated hydrocarbon in the aforementioned method and system embodiments is C2-C10 alkene or C2-C5 alkene. In some embodiments of the methods and systems described as above, the unsaturated hydrocarbon in the aforementioned embodiments and as described herein is, ethylene. The halohydrocarbon formed from such unsaturated hydrocarbon is, e.g., ethylene dichloride, chloroethanol, propylene dichloride, propylene chlorohydrin, butyl chloride, dichlorobutane, chlorobutanol, etc. In some embodiments of the methods and systems described as above, the metal ion in the metal halide is a metal ion described herein, such as, but not limited to, copper, iron, tin, or chromium.

In some embodiments, the unsaturated hydrocarbon is ethylene and the methods comprise reacting ethylene with the metal halide in the higher oxidation state, e.g. $CuCl_2$ and the one or more lanthanide halides, e.g. $CeCl_3$ in the anode electrolyte, to result in one or more products comprising EDC. In some embodiments, the one or more products further comprise chloroethanol (CE). In some embodiments, the method further comprises forming ethylene oxide from chloroethanol.

In some embodiments, the unsaturated hydrocarbon is propylene and the methods comprise reacting propylene with the metal halide in the higher oxidation state, e.g. $CuCl_2$ and the one or more lanthanide halides, e.g. $CeCl_3$ in the anode electrolyte, to result in one or more products comprising propylene dichloride. In some embodiments, the one or more products further comprise propylene chlorohydrin (PCH). In some embodiments, the method further comprises forming propylene oxide from PCH.

The formation of ethylene oxide from CE and/or formation of propylene oxide from PCH have been described in detail in U.S. Provisional Patent Application No. 62/528,273, filed Jul. 3, 2017, which is incorporated herein by reference in its entirety.

The ethylene dichloride formed by the methods and systems of the invention can be used for any commercial purposes. In some embodiments, the ethylene dichloride is subjected to vinyl chloride monomer (VCM) formation through the process such as cracking/purification. The vinyl chloride monomer may be used in the production of polyvinylchloride. In some embodiments, the hydrochloric acid formed during the conversion of EDC to VCM may be separated and reacted with acetylene to further form VCM.

In some embodiments, the HCl generated in the process of VCM formation may be circulated to one or more of the electrochemical systems described herein where HCl is used in the cathode or anode electrolyte to form hydrogen gas or water at the cathode. Any of the electrochemical systems of the invention such as system illustrated in FIGS. 1 and 2 may be used to form $CuCl_2$ which when reacted with ethylene along with the one or more lanthanide halides results in EDC. The cracking of EDC with subsequent processing of VCM produces HCl which may be circulated to any of the electrochemical systems of FIGS. 1 and 2 to further form $CuCl_2$.

In some embodiments, the chlorination of ethylene in an aqueous medium with metal chloride in the higher oxidation state and cerium chloride, results in ethylene dichloride, chloroethanol, or combination thereof.

In some embodiments of the methods and systems described herein, there is a formation of more than 10 wt %; or more than 20 wt %, or more than 30 wt %, or more than 40 wt %, or more than 50 wt %, or more than 60 wt %, or more than 70 wt %, or more than 80 wt %, or more than 90 wt %, or more than 95 wt %, or about 99 wt %, or between about 10-99 wt %, or between about 10-95 wt %, or between about 15-95 wt %, or between about 25-95 wt %, or between about 50-95 wt %, or between about 50-99 wt %, or between about 50-99.9 wt %, or between about 50-99.99 wt % ethylene dichloride, from ethylene in the presence of the one or more lanthanide halides. In some embodiments, the remaining weight percentage is of chloroethanol. In some embodiments, no chloroethanol is formed in the reaction. In some embodiments, less than 0.001 wt % or less than 0.01 wt % or less than 0.1 wt % or less than 0.5 wt % or less than 1 wt % or less than 5 wt % or less than 10 wt % or less than 20 wt % of chloroethanol is formed with the remaining EDC in the reaction. In some embodiments, less than 0.001 wt % or less than 0.01 wt % or less than 0.1 wt % or less than 0.5 wt % or less than 1 wt % or less than 5 wt % of metal ion is present in EDC product. In some embodiments, less than 0.001 wt % or less than 0.01 wt % or less than 0.1 wt % of chloroethanol and/or metal ion is present in the EDC product.

In some embodiments, the EDC product containing the metal ion may be subjected to washing step which may include rinsing with an organic solvent or passing the EDC product through a column to remove the metal ions. In some embodiments, the EDC product may be purified by distillation where any of the side products such as chloral ($CCl_3CHO$) and/or chloral hydrate (2,2,2-trichloroethane-1,1-diol), if formed, may be separated.

In some embodiments, the unsaturated hydrocarbon is propene. In some embodiments, the metal ion in the higher oxidation state such as $CuCl_2$ and the one or more lanthanide halides is treated with propene to result in propane dichloride ($C_3H_6Cl_2$) or dichloropropane (DCP) which can be used to make allyl chloride ($C_3H_5Cl$). In some embodiments, DCP may be formed along with PCH or DCP may be converted to PCH. The PCH may further be used to make propylene oxide (as described above).

In some embodiments, the unsaturated hydrocarbon is butane or butylene. In some embodiments, the metal ion in the higher oxidation state such as $CuCl_2$ and the one or more lanthanide halides is treated with butene to result in butane dichloride ($C_4H_8Cl_2$) or dichlorobutene ($C_4H_6Cl_2$) which can be used to make chloroprene ($C_4H_5Cl$). In some embodiments, the unsaturated hydrocarbon is benzene. In some embodiments, the metal ion in the higher oxidation state such as $CuCl_2$ and the one or more lanthanide halides is treated with benzene to result in chlorobenzene. In some embodiments, the metal ion in the higher oxidation state such as $CuCl_2$ and the one or more lanthanide halides is treated with acetylene to result in chloroacetylene, dichloroacetylene, vinyl chloride, dichloroethene, tetrachloroethene, or combination thereof. In some embodiments, the unsaturated hydrocarbon is treated with metal chloride in higher oxidation state and the one or more lanthanide halides to form a product including, but not limited to, ethylene dichloride, chloroethanol, chloropropene, propylene oxide, allyl chloride, methyl chloride, trichloroethylene, tetrachloroethene, chlorobenzene, 1,2-dichloroethane, 1,1,2-trichloroethane, 1,1,2,2-tetrachloroethane, pentachloroethane, 1,1-dichloroethene, chlorophenol, chlorinated toluene, etc. In some embodiments, the unsaturated hydrocarbon is treated with metal chloride in higher oxidation state and the one or more lanthanide halides to form a product including, but not limited to, ethylene dichloride, chloroethanol, and one or more products selected from the group consisting of substituted or unsubstituted dioxane, substituted or unsubstituted dioxolane, dichloroethylether, dichloromethyl methyl ether, dichloroethyl methyl ether, chloroform, carbon tetrachloride, phosgene, and combinations thereof. The formation of products selected from the group consisting of substituted or unsubstituted dioxane, substituted or unsubstituted dioxolane, dichloroethylether, dichloromethyl methyl ether, dichloroethyl methyl ether, chloroform, carbon tetrachloride, phosgene, and combinations thereof, have been described in detail in U.S. patent application Ser. No. 14/855,262, filed Sep. 15, 2015, which is incorporated herein by reference in its entirety in the present disclosure.

In some embodiments, the yield of the halogenated hydrocarbon or halohydrocarbon from unsaturated hydrocarbon, e.g. the yield of EDC from ethylene or yield of DCP from propylene, or dichlorobutene from butene, using the metal ions and the one or more lanthanide halides is more than 90% or more than 95% or between 90-95% or between 90-99% or between 90-99.9% by weight. In some embodiments, the selectivity of the halogenated hydrocarbon from unsaturated hydrocarbon, e.g. the yield of EDC from ethylene or yield of DCP from propylene, or dichlorobutene from butene, using the metal ions and the one or more lanthanide halides is more than 80% or more than 90% or between 80-99% by weight. In some embodiments, the STY (space time yield) of the halogenated hydrocarbon from unsaturated hydrocarbon, e.g. the yield of EDC from ethylene or yield of DCP from propylene, or dichlorobutene from butene, using the metal ions and the one or more lanthanide halides is more than 0.5 or more than 1.

In some embodiments, the metal formed with a higher oxidation state and the one or more lanthanide halides in the anode electrolyte of the electrochemical systems of FIGS. 1 and 2 may be reacted with saturated hydrocarbons to from corresponding halohydrocarbons. For example, the metal chloride, metal bromide, metal iodide, etc. may result in corresponding chlorohydrocarbons, bromohydrocarbons, or iodohydrocarbons, after the reaction of the saturated hydrocarbons with the metal halide and the one or more lanthanide halides. In some embodiments, the reaction of metal halide and the one or more lanthanide halides with the saturated hydrocarbons results in the generation of the above described products as well as the metal halide in the lower oxidation state. The aqueous medium containing the metal ion in the lower oxidation state may then be re-circulated back to the electrochemical system for the generation of the metal ion in the higher oxidation state.

The "saturated hydrocarbon" as used herein, includes a hydrocarbon with no unsaturated carbon or hydrocarbon. The hydrocarbon may be linear, branched, or cyclic. For example, the hydrocarbon may be substituted or unsubstituted alkanes and/or substituted or unsubstituted cycloalkanes. The hydrocarbons may have a general formula of an unsubstituted alkane as $C_nH_{2n+2}$ where n is 2-20 or 2-10 or 2-8, or 2-5. In some embodiments, one or more hydrogens on the alkane or the cycloalkanes may be further substituted with other functional groups such as but not limited to, halogen (including chloro, bromo, iodo, and fluoro), carboxylic acid (—COOH), hydroxyl (—OH), amines, etc.

Examples of substituted or unsubstituted alkanes include, but not limited to, methane, ethane, chloroethane, bromoethane, iodoethane, propane, chloropropane, hydroxypropane, butane, chlorobutane, hydroxybutane, pentane, hexane, cyclohexane, cyclopentane, chlorocyclopentane, etc.

In some embodiments, the saturated hydrocarbon in the aforementioned embodiments is C2-C10 alkane or C2-C5 alkane. In some embodiments, the saturated hydrocarbon in the aforementioned embodiments and as described herein is, methane. In some embodiments, the saturated hydrocarbon in the aforementioned embodiments and as described herein is, ethane. In some embodiments, the saturated hydrocarbon in the aforementioned embodiments and as described herein is, propane. The halohydrocarbon formed from such saturated hydrocarbon is, e.g., chloromethane, dichloromethane, chloroethane, dichloroethane, chloropropane, dichloropropane, etc.

It is to be understood that the example of the electrochemical system illustrated in FIGS. 1 and 2 can be configured for saturated hydrocarbons by replacing the unsaturated hydrocarbon with a saturated hydrocarbon.

In some embodiments, the chlorination of ethane in an aqueous medium with metal chloride in the higher oxidation state and the one or more lanthanide halides, results in ethane chloride, ethane dichloride, or combination thereof. In some embodiments of the methods and systems described herein, there is a formation of more than 50 wt %, or more than 60 wt %, or more than 70 wt %, or more than 80 wt %, or more than 90 wt %, or more than 95 wt %, or about 99 wt %, or between about 50-95 wt %, or between about 50-99 wt %, or between about 50-99.9 wt %, or between about 50-99.99 wt % chloroethane, from ethane. In some embodiments, the remaining weight percentage is of chloroethanol and/or ethylene dichloride. In some embodiments, no chloroethanol is formed in the reaction. In some embodiments, less than 0.001 wt % or less than 0.01 wt % or less than 0.1 wt % or less than 0.5 wt % or less than 1 wt % or less than 5 wt % or less than 10 wt % or less than 20 wt % of chloroethanol is formed with the remaining product in the reaction. In some embodiments, less than 0.001 wt % or less than 0.01 wt % or less than 0.1 wt % or less than 0.5 wt % or less than 1 wt % or less than 5 wt % of metal ion is present in the product. In some embodiments, less than 0.001 wt % or less than 0.01 wt % or less than 0.1 wt % of chloroethanol and/or metal ion is present in the product.

In some embodiments, the yield of the halogenated hydrocarbon from saturated hydrocarbon, e.g. the yield of chloroethane and/or EDC from ethane, using the metal ions and the one or more lanthanide halides is more than 90% or more than 95% or between 90-95% or between 90-99% or between 90-99.9% by weight. In some embodiments, the selectivity of the halogenated hydrocarbon from saturated hydrocarbon, e.g. the yield of chloroethane and/or EDC from ethane, using the metal ions and the one or more lanthanide halides is more than 80% or more than 90% or between 80-99% by weight. In some embodiments, the STY (space time yield) of the halogenated hydrocarbon from saturated hydrocarbon is more than 0.5 or more than 1.

The halogenation reaction is carried out in systems including a reactor operably connected to the anode chamber. The reactor may be configured to contact the metal halide and the one or more lanthanide halides in the anode electrolyte with the unsaturated or saturated hydrocarbon. The reactor may be any means for contacting the metal halide and the one or more lanthanide halides in the anode electrolyte with the unsaturated or saturated hydrocarbon. Such means or such reactor are well known in the art and include, but not limited to, pipe, duct, tank, series of tanks, container, tower, conduit, and the like. The reactor may be equipped with one or more of controllers to control temperature sensor, pressure sensor, control mechanisms, inert gas injector, etc. to monitor, control, and/or facilitate the reaction. In some embodiments, the reaction between the metal halide with metal ion in higher oxidation state and the one or more lanthanide halides with the unsaturated or saturated hydrocarbon, are carried out in the reactor at the temperature of between 100-200° C. or between 100-175° C. or between 150-175° C. and pressure of between 100-500 psig or between 100-400 psig or between 100-300 psig or between 150-350 psig.

In some embodiments, the electrochemical system and the reactor are inside the same unit and are connected inside the unit. For example, in some embodiments, the anode electrolyte, containing the metal ion in the higher oxidation state, the metal ion in the lower oxidation state, and the one or more lanthanide halides (optionally salt), along with ethylene are fed to a prestressed (e.g., brick-lined) reactor. The chlorination of ethylene may take place inside the reactor to form ethylene dichloride (EDC or dichloroethane DCE) and the metal ion in the lower oxidation state. The reactor may operate in the range of 340-360° F. and 200-300 psig. Other reactor conditions, such as, but not limited to, metal ion concentration, the one or more lanthanide halides concentration, salt concentration, ratio of metal ion in the lower oxidation state to the metal ion in the higher oxidation state, partial pressures of DCE and water vapor can be set to assure high selectivity operation. Reaction heat may be removed by vaporizing water. In some embodiments, a cooling surface may not be required in the reactor and thus no temperature gradients or close temperature control may be needed. The reactor effluent gases may be quenched with water in the prestressed (e.g., brick-lined) packed tower. The liquid leaving the tower maybe cooled further and separated into the aqueous phase and DCE phase. The aqueous phase may be split part being recycled to the tower as quench water and the remainder may be recycled to the reactor or the electrochemical system. The DCE product may be cooled further and flashed to separate out more water and dissolved ethylene. This dissolved ethylene may be recycled. The construction material of the plant may include prestressed brick linings, Hastealloys B and C, inconel, dopant grade titanium (e.g. AKOT, Grade II, Grade VII, and the like), tantalum, Kynar, Teflon, PEEK, glass, or other polymers or plastics. The reactor may also be designed to continuously flow the anode electrolyte in and out of the reactor.

The processes and systems described herein may be batch processes or systems or continuous flow processes or systems.

In some embodiments, the reaction of the metal ion in the higher oxidation state and the one or more lanthanide halides with the unsaturated or saturated hydrocarbon may take place when the reaction temperature is above 50° C. up to 350° C. In aqueous media, the reaction may be carried out under a super atmospheric pressure of up to 1000 psi or less to maintain the reaction medium in liquid phase at a temperature of from 50° C. to 200° C., typically from about 120° C. to about 180° C.

The unsaturated or saturated hydrocarbon feedstock may be fed to the halogenation vessel continuously or intermittently. Efficient halogenation may be dependent upon achieving intimate contact between the feedstock and the anolyte and the halogenation reaction may be carried out by a technique designed to improve or maximize such contact. The metal ion and the one or more lanthanide halides solution may be agitated by stirring or shaking or any desired technique, e.g. the reaction may be carried out in a column, such as a packed column, or a trickle-bed reactor or reactors described herein. For example, where the unsaturated or saturated hydrocarbon is gaseous, a counter-current technique may be employed wherein the unsaturated or saturated hydrocarbon is passed upwardly through a column or reactor and the metal ion solution is passed downwardly through the column or reactor. In addition to enhancing contact of the unsaturated or saturated hydrocarbon and the metal ion in the solution, the techniques described herein may also enhance the rate of dissolution of the unsaturated or saturated hydrocarbon in the solution, as may be desirable in the case where the solution is aqueous and the water-solubility of the unsaturated or saturated hydrocarbon is low. Dissolution of the feedstock may also be assisted by higher pressures.

Mixtures of saturated, unsaturated hydrocarbons and/or partially halogenated hydrocarbons may be employed. In some embodiments, partially-halogenated products of the process of the invention which are capable of further halogenation may be recirculated to the reaction vessel through a product-recovery stage and, if appropriate, a metal ion in the lower oxidation state regeneration stage. In some embodiments, the halogenation reaction may continue outside the halogenation reaction vessel, for example in a separate regeneration vessel, and care may need to be exercised in controlling the reaction to avoid over-halogenation of the unsaturated or saturated hydrocarbon.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Various modifications of the invention in addition to those described herein will become apparent to those skilled in the art from the foregoing description and accompanying figures. Such modifications fall within the scope of the appended claims. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

In the examples and elsewhere, abbreviations have the following meanings:

| | |
|---|---|
| AEM = | anion exchange membrane |
| $cm^2$ = | centimeter square |
| EDC = | ethylene dichloride |
| g = | gram |
| GC = | gas chromatography |
| HCl = | hydrochloric acid |
| hr or h = | hour |
| L = | liter |
| M = | molar |
| mA = | milliamps |
| $mA/cm^2$ = | milliamps/centimeter square |
| mg = | milligram |
| min. = | minute |
| mmol = | millimole |
| mol = | mole |
| mL = | milliliter |
| NaCl = | sodium chloride |
| NaOH = | sodium hydroxide |
| STY = | space time yield |
| TOC = | total organic carbon |
| V = | voltage |
| w/v = | weight/volume |
| w/w = | weight/weight |

EXAMPLES

Example 1

Effects of $CeCl_3$ on Selectivity and STY of the Product

In this experiment, $CeCl_3$ was used in the $CuCl_x$/NaCl anolyte system to investigate its effect on selectivity and STY of EDC formed from the chlorination of ethylene.

Procedure:

The experiment was conducted in a stirred pressure vessel. The pressure vessel was heated with an outer jacket. The reactor was equipped with a gas inlet and outlet. A temperature probe was used to measure the reaction temperature in the solution. A 115-135 mL mixture of metal chlorides and water was placed into a glass-lined 450 mL stirred pressure vessel. After purging the closed reactor with $N_2$, it was heated to 150° C. After reaching this temperature, ethylene was added to a total pressure of 200 psi through a back pressure controller and a steady gas flow of 4 slpm was established. The stir rate was 1300 rpm during the reactor time. The gas outlet flow was bubbled through 200 mL ethyl acetate that was kept at low temperature with an ice bath. After a 15 min reaction time, the reactor was cooled. The gas flow and stirring were continued for 5 min after cooling was initiated. After reaching 100° C., the remaining headspace gas was purged with $N_2$ through the ethyl acetate bubbler.

The ethyl acetate phase of the bubbler was analyzed by GC (gas chromatography) and contained the majority of EDC. The remaining aqueous solution in the reactor was analyzed by TOC (total organic content) and extracted with ethyl acetate. The ethyl acetate fraction was also analyzed by GC.

The STY was determined by the total amount EDC in the bubbler and remaining aqueous solution on a mol basis divided by the reaction time and reaction volume. The selectivity was determined by the total amount of EDC in the bubbler and remaining aqueous solution on a mol basis divided by the total amount of products on a C2 basis as determined by GC and TOC.

Solubility was determined visually after heating mixtures to 90° C.

The compositions with increasing $CeCl_3$ concentrations were tested and are as shown in Tables I-III Observations:

The experiment showed that $CeCl_3$ significantly outperformed the NaCl anolyte system (without $CeCl_3$) on both selectivity and EDC STY basis. The selectivity improvement was the result of much higher EDC production while maintaining a relatively unchanged overall byproduct content. The data set shown in Table III with highest $CeCl_3$ concentration yielded an EDC selectivity of 94.7%—progressively higher than the selectivity of 92.1% observed for the system without $CeCl_3$ shown in Table I (see also Table IV below). It was observed that at static operating conditions, $CeCl_3$ increases EDC production rate while maintaining stable byproduct content across a sizeable range of $CeCl_3$ substitutions.

TABLE I

|  | g | mol % |
| --- | --- | --- |
| CuCl | 18.5094 | 2.9% |
| $CuCl_2 \cdot 2H_2O$ | 119.5694 | 11.0% |
| NaCl | 32.7364 | 8.8% |
| $CeCl_3 \cdot 7H_2O$ | 0 | 0.0% |
| Cl- | 76.3206 | 33.9% |
| $H_2O$, tot | 88.1929 | 77.2% |

TABLE II

|  | g | mol % |
| --- | --- | --- |
| CuCl | 18.5930 | 3.0% |
| $CuCl_2 \cdot 2H_2O$ | 119.6636 | 11.0% |
| NaCl | 27.9339 | 7.5% |
| $CeCl_3 \cdot 7H_2O$ | 31.3914 | 1.3% |
| Cl- | 82.4455 | 36.5% |
| $H_2O$, tot | 88.2969 | 77.2% |

TABLE III

|  | g | mol % |
| --- | --- | --- |
| CuCl | 18.6019 | 2.9% |
| $CuCl_2 \cdot 2H_2O$ | 119.6440 | 11.0% |
| NaCl | 24.6224 | 6.6% |
| $CeCl_3 \cdot 7H_2O$ | 52.3709 | 2.2% |
| Cl- | 86.4258 | 38.2% |
| $H_2O$, tot | 88.6246 | 77.2% |

TABLE IV

| $CeCl_3$ |  | Table I | Table II | Table III |
| --- | --- | --- | --- | --- |
| Ethylene dichloride | mmol | 27.78 | 31.55 | 38.75 |
| Chloroethanol | mmol | 0.44 | 0.13 | 0.05 |
| trichloroacetaldehyde | mmol | 0.22 | 0.18 | 0.21 |
| dichloroacetaldehyde | mmol | 0.05 | 0.00 | 0.02 |
| Total Byproducts as measured by GC and TOC | mmol (as C2) | 2.37 | 2.40 | 2.16 |
| Selectivity | % | 92.1% | 92.9% | 94.7% |
| STY | molEDC/L/h | 0.82 | 0.96 | 1.16 |

Example 2

Effects of $CeCl_3$ on Temperature of the Reaction

In this experiment, $CeCl_3$ was investigated in the $CuCl_x$/NaCl anolyte system of Table II as above, at 140° C. and 160° C. (data for 150° C. shown in Example 1). The procedure for this experiment was similar to the procedure outlined in Example 1. This temperature-dependent data shows that slightly higher selectivity at 140° C. was achieved as compared to 150° C. and 160° C. (93.2%, 92.9%, and 92.0%, respectively). Therefore, $CeCl_3$ facilitates similar or higher selectivity even at lower temperatures making the process more economical and environmentally friendly.

Example 3

Effects of $CeCl_3$ on Voltage of the Electrochemical Cell

In this experiment, $CeCl_3$ was used in the $CuCl_x$/NaCl anolyte system to investigate its effect on the voltage of the electrochemical cell. The procedure for the electrochemical reaction is provided below.

The standard lab cell had an active area of 4 cm width by 10 cm height. The cell had three electrolyte chambers and contained an anode, cathode, anion exchange membrane, and cation exchange membrane. The anode was constructed of a titanium-base corrugated expanded mesh with a welded fine expanded mesh of PGM coated titanium. The cathode was constructed of a coarse stainless steel expanded mesh with a welded fine mesh of PGM coated nickel. The anode and cathode compartments were operated under zero-gap conditions and the intermediate compartment had a thickness of approximately 1 mm. All electrolytes were preheated to 90° C. The flow-rates of the anolyte, brine, and catholyte were 20 kgh, 7 kgh, and 7 kgh respectively. 1 psi back pressure was applied to the brine to maintain zero gap in the anode and cathode compartments. A standard galvanostatic step and hold test was conducted. Current was ramped from 25 mA/cm² to the full operating current of 300 mA/cm². Cell voltages were monitored and recorded throughout the test run.

Table V shows Experiment No. 1 with no cerium chloride and Experiment No. 2 with 3.49 mol % $CeCl_3$. Experiment No. 2 shows an improved voltage over Experiment No. 1. The addition of $CeCl_3$ facilitates voltage improvement while retaining solubility at 90° C.

TABLE V

|  |  | Experiment No. | |
|---|---|---|---|
|  |  | 1 | 2 |
| CuCl | mol % | 1.94 | 2.65 |
| $CuCl_2$ | mol % | 10.74 | 7.35 |
| NaCl | mol % | 7.75 | 2.99 |
| $CeCl_3$ | mol % | 0 | 3.49 |
| $H_2O$ | mol % | 79.58 | 83.52 |
| E-Chem Voltage | V | 2.77 | 2.71 |

Example 4

Effects of $LaCl_3$ and $CeCl_3$ on Selectivity and STY of the Product

In this experiment, $LaCl_3$ and $CeCl_3$ were used in the $CuCl_x$/NaCl anolyte system (compositions shown in Table VI and VII) to investigate its effect on the selectivity and STY of EDC formed from the chlorination of ethylene. The procedure used was as described in Example 1.

TABLE VI

|  | g | mol % |
|---|---|---|
| CuCl | 12.2345 | 2.1 |
| $CuCl_2 \cdot 2H_2O$ | 80.0607 | 8.0 |
| NaCl | 10.2882 | 3.0 |
| $LaCl_3 \cdot 7H_2O$ | 76.4371 | 3.5 |
| Cl– | 66.15 | 24.0 |
| $H_2O$, add | 45.35 | 42.9 |
| $H_2O$, tot | 88.1949 | 83.4 |

TABLE VII

|  | g | mol % |
|---|---|---|
| CuCl | 12.1244 | 2.1 |
| $CuCl_2 \cdot 2H_2O$ | 79.5200 | 8.0 |
| NaCl | 10.2321 | 3.0 |
| $CeCl_3 \cdot 7H_2O$ | 76.0743 | 3.5 |
| Cl– | 65.44 | 24.0 |
| $H_2O$, add | 45.0568 | 42.9 |
| $H_2O$, tot | 87.5759 | 83.4 |

TABLE VIII

| No LAH | | |
|---|---|---|
|  | g | mol % |
| CuCl | 11.88 | 2.2 |
| $CuCl_2 \cdot 2H_2O$ | 102.29 | 11.1 |
| NaCl | 21.0384 | 6.7 |
| Cl– | 59.556 | 23.7 |
| $H_2O$, add | 56.0934 | 57.8 |
| $H_2O$, tot | 77.69 | 80.0 |

TABLE IX

|  |  | $LaCl_3$ (Table VI) | $CeCl_3$ (Table VII) | No LAH (Table VIII) |
|---|---|---|---|---|
| Ethylene dichloride | mmol | 19.02 | 21.33 | 21.70 |
| Chloroethanol | mmol | 0.82 | 0.46 | 1.73 |
| trichloroacetaldehyde | mmol | 0.14 | 0.1 | 0.21 |
| dichloroacetaldehyde | mmol | 0.0 | 0.0 | 0.08 |
| Total Byproducts as measured by GC and TOC | mmol (as C2) | 1.27 | 1.22 | 2.71 |
| Selectivity | % | 93.5 | 94.5 | 86.7 |
| STY | molEDC/L/h | 0.62 | 0.72 | 0.64 |

Observations:

As shown in Table IX, the experiment shows that $LaCl_3$ and $CeCl_3$ containing anolyte achieve a higher selectivity compared to the anolyte containing no LAH.

What is claimed is:

1. A method, comprising:
   contacting an anode with an anode electrolyte wherein the anode electrolyte comprises metal halide, one or more lanthanide halides, and water wherein the one or more lanthanide halides are in concentration range of between about 0.4-10 mol %;
   contacting cathode with a cathode electrolyte;
   applying voltage to the anode and the cathode and oxidizing the metal halide from a lower oxidation state to a higher oxidation state at the anode; and
   reacting an unsaturated hydrocarbon or a saturated hydrocarbon with the metal halide in the higher oxidation state and the one or more lanthanide halides in the anode electrolyte, to result in one or more products comprising halohydrocarbon.

2. The method of claim 1, wherein lanthanide in the lanthanide halide is selected from the group consisting of lanthanum, cerium, praseodymium, neodymium, promethium, samarium, europium, gadolinium, terbium, dysprosium, holmium, erbium, thulium, ytterbium, lutetium, and combinations thereof.

3. The method of claim 1, wherein the lanthanide halide is cerium halide and/or lanthanum halide.

4. The method of claim 3, wherein the cerium halide is $CeCl_3 \cdot 7H_2O$.

5. The method of claim 1, wherein the anode electrolyte further comprises salt.

6. The method of claim 1, wherein the one or more lanthanide halides result in more than 90% selectivity of the halohydrocarbon.

7. The method of claim 1, wherein the one or more lanthanide halides reduce temperature of the reaction by more than 5° C. with substantially same or higher selectivity and/or space time yield (STY) of the halohydrocarbon as compared to when no lanthanide halide is used.

8. The method of claim 1, wherein the metal halide in the lower oxidation state and the metal halide in the higher oxidation state is CuCl and $CuCl_2$, respectively.

9. The method of claim 1, wherein the unsaturated hydrocarbon is a C2-C10 alkene or the saturated hydrocarbon is C2-C10 alkane.

10. The method of claim 1, wherein the unsaturated hydrocarbon is ethylene, propylene, or butylene which reacts with the anode electrolyte comprising the metal halide in the higher oxidation state and the one or more lanthanide halides to form one or more products comprising ethylene dichloride, propylene dichloride or 1,4-dichlorobutane, respectively.

11. The method of claim 1, wherein the saturated hydrocarbon is methane, ethane, propane, or butane which reacts with the anode electrolyte comprising the metal halide in the higher oxidation state and the one or more lanthanide halides to form one or more products comprising dichloro methane, ethylene dichloride, propylene dichloride or 1,4-dichlorobutane, respectively.

12. The method of claim 1, further comprising forming an alkali, water, or hydrogen gas at the cathode.

13. The method of claim 1, wherein the cathode electrolyte comprises water and the cathode is an oxygen depolarizing cathode that reduces oxygen and water to hydroxide ions;
the cathode electrolyte comprises water and the cathode is a hydrogen gas producing cathode that reduces water to hydrogen gas and hydroxide ions; the cathode electrolyte comprises hydrochloric acid and the cathode is a hydrogen gas producing cathode that reduces hydrochloric acid to hydrogen gas; or the cathode electrolyte comprises hydrochloric acid and the cathode is an oxygen depolarizing cathode that reacts hydrochloric acid and oxygen gas to form water.

14. The method of claim 1, wherein metal ion in the metal halide is selected from the group consisting of iron, chromium, copper, tin, silver, cobalt, uranium, lead, mercury, vanadium, bismuth, titanium, ruthenium, osmium, europium, zinc, cadmium, gold, nickel, palladium, platinum, rhodium, iridium, manganese, technetium, rhenium, molybdenum, tungsten, niobium, tantalum, zirconium, hafnium, and combination thereof.

15. The method of claim 1, wherein metal ion in the metal halide is copper.

16. The method of claim 1, wherein metal ion in the metal halide is copper that is converted from $Cu^+$ to $Cu^{2+}$, metal ion in the metal halide is iron that is converted from $Fe^{2+}$ to $Fe^{3+}$, metal ion in the metal halide is tin that is converted from $Sn^{2+}$ to $Sn^{4+}$, metal ion in the metal halide is chromium that is converted from $Cr^{2+}$ to $Cr^{3+}$, metal ion in the metal halide is platinum that is converted from $Pt^{2+}$ to $Pt^{4+}$, or combination thereof.

17. A method, comprising:
contacting an anode with an anode electrolyte wherein the anode electrolyte comprises copper (I) chloride, copper (II) chloride, sodium chloride, cerium (III) chloride, and water;
contacting cathode with a cathode electrolyte;
applying voltage to the anode and the cathode and oxidizing the copper (I) chloride to copper (II) chloride at the anode; and
reacting an unsaturated hydrocarbon or a saturated hydrocarbon with the copper (II) chloride and the cerium (III) chloride in the anode electrolyte, to result in one or more products comprising halohydrocarbon.

* * * * *